US007659104B2

(12) United States Patent
Bramucci et al.

(10) Patent No.: US 7,659,104 B2
(45) Date of Patent: Feb. 9, 2010

(54) SOLVENT TOLERANT MICROORGANISMS AND METHODS OF ISOLATION

(75) Inventors: Michael G. Bramucci, Boothwyn, PA (US); Vasantha Nagarajan, Wilmington, DE (US); Natalia Sedkova, Cherry Hill, NJ (US); Manjari Singh, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/743,220

(22) Filed: May 2, 2007

(65) Prior Publication Data
US 2007/0259411 A1    Nov. 8, 2007

Related U.S. Application Data

(60) Provisional application No. 60/798,417, filed on May 5, 2006.

(51) Int. Cl.
C12N 1/20 (2006.01)
C12P 7/16 (2006.01)
C12N 1/21 (2006.01)
C12N 1/00 (2006.01)
C12N 1/32 (2006.01)

(52) U.S. Cl. .................... 435/252.1; 435/160; 435/243; 435/247; 435/252.3

(58) Field of Classification Search ................. 435/160, 435/243, 247, 252.1, 252.3
See application file for complete search history.

(56) References Cited

U.S. PATENT DOCUMENTS

| 4,424,275 | A  | 1/1984  | Levy            |
| 4,568,643 | A  | 2/1986  | Levy            |
| 4,757,010 | A  | 7/1988  | Hermann et al.  |
| 5,192,673 | A  | 3/1993  | Jain et al.     |
| 5,210,032 | A  | 5/1993  | Kashket         |
| 6,358,717 | B1 | 3/2002  | Blaschek et al. |
| 6,960,465 | B1 | 11/2005 | Papoutsakis et al. |
| 2002/0028492 | A1 | 3/2002 | Lenke et al.   |
| 2003/0016227 | A1 | 1/2003 | Matthies       |
| 2007/0218533 | A1 | 9/2007 | Gill et al.    |

FOREIGN PATENT DOCUMENTS

| CA | 2039245       | 4/1990  |
| EP | 0 112 459 A1  | 7/1984  |
| EP | 0 282 474 A1  | 9/1988  |
| EP | 0 315 949 A2  | 5/1989  |
| EP | 0 645 453 B1  | 3/1995  |
| EP | 1 149 918 A1  | 10/2001 |
| JP | 61-209594     | 9/1986  |
| JP | 63-102687     | 5/1988  |
| JP | 63-254986     | 10/1988 |
| WO | WO 90/02193 A1 | 3/1990 |
| WO | WO 98/51813 A1 | 11/1998 |
| WO | WO 03/078615 A1 | 9/2003 |

OTHER PUBLICATIONS

Qureshi et al., Journal of Industrial Microbiology and Biotechnology 27:287-291, 2001.*
Butanols, Ullmann'S Encyclopedia of Industrial Chemistry, $6^{TH}$ Edition, 2003, vol. 5:716-719.
Carlini et al., Guerbet Condensation of Methanol With N-Propanol to Isobutyl Alcohol Over Heterogeneous Copper Chromite/Mg-Al Mixed Oxides Catalysts, J. Molec. Catal. A: Chem., 2004, vol. 220:215-220.
Girbal et al., Regulation of Solvent Production in *Clostridium acetobutylicum*, Trends in Biotechnology, 1998, vol. 16:11-16.
Tomas et al., Overexpression of groESL in *Clostridium acetobutylicum* Results in Increased Solvent Production and Tolerance, Prolonged Metabolism, and Changes in the Cell's Transcriptional Program, Appl. Environ. Microbiol., 2003, vol. 69:4951-4965.
Quratulain et al., Development and Characterization of Butanol Resistant Strain of *Clostridium acetobutylicum* in Molasses Medium, Folia Microbiologica, 1995, vol. 40:467-471.
Soucaille et al., Butanol Tolerance and Autobacteriocin Production by *Clostridium acetobutylicum*, Current Microbiology, 1987, vol. 14:295-299.
Desmond et al., Improved Stress Tolerance of Gro-ESL Overproducing *Lactococcus lactic* and Probiotic *Lactobacillus paracasei* NFBC 338, Appl. Environ. Microbiol., 2004, vol. 70:5929-5936.
Sardessai et al., Organic Solvent-Tolerant Bacteria in Mangrove Ecosystem, Current Science, 2002, vol. 82:622-623.
Bieszkiewicz et al., Studies on the Resistance of Activated Sludge Bacteria to High Concentrations of Metanol, Butanol, Glycol, Cyclohexanone and Cyclohexylamine, Acta Microbiologica Polonica, 1987, vol. 36:259-265.
Underwood et al., Genetic Changes to Optimize Carbon Partitioning Between Ethanol and Biosynthesis in Ethanologenic *Escherichia coli*, Appl. Environ. Microbiol., 2002, vol. 68:6263-6272.
Bermejo et al., Expression of Clostridium Acetobutylicum ATCC 824 Genes in *Escherichia coli* for Acetone Production and Acetate Detoxification, Applied & Environmental Microbiology, 1998, vol. 64:1079-1085.
Veeranagouda, Yaligara et al., Enterobacter sp. VKGH12 growing with n-butanol as the sole carbon source and cells to which the alcohol is added as pure toxin show considerable differences in their adaptive responses, FEMS Microbiology Letters, 2006, pp. 48-54, vol. 254, Federation of European Microbiological Societies.
Couto, Jose Antonio et al., Enhancement of apparent resistance to ethanol in *Lactobacillus hilgardii*, Biotechnology Letters, May 1997, pp. 487-490, vol. 19, No. 5.
Speranza, Giovanna et al., Conversion of meso-2,3-Butanediol into 2-Butanol by Lactobacilli. Stereochemical and Enzymatic Aspects, Journal of Agricultural and Food Chemistry, 1997, pp. 3476-3480, vol. 45, American Chemical Society.

(Continued)

Primary Examiner—Delia M Ramirez
(74) Attorney, Agent, or Firm—Christine M. Lhulier

(57) ABSTRACT

*Enterococcus* bacteria having enhanced tolerance to butanols have been isolated. The bacteria are useful for the fermentive production of butanol. New methods for the isolation of butanol tolerant *Enterococcus* are also provided.

2 Claims, No Drawings

OTHER PUBLICATIONS

International Search Report dated Mar. 18, 2008, International Application No. PCT/2007/010815.

U.S. Appl. No. 11/527,995, filed Sep. 27, 2006, Gail K. Donaldson et al.

U.S. Appl. No. 60/796,816, filed May 2, 2006, Gail K. Donaldson et al.

U.S. Appl. No. 11/586,315, filed Oct. 25, 2006, Gail K. Donaldson et al.

Fontaine et al., Molecular Characterization and Transcriptional Analysis of ADHE2, The Gene Encoding the NADH-Dependent Aldehyde/Alcohol Dehydrogenase Responsible for Butanol Production in Alcohologenic Cultures of *Clostridium acetobutylicum* ATCC-824, Journal of Bacteriology, 2002, vol. 184:821-830.

Cornillot et al., The Genes for Butanol and Acetone Formation in *Clostridium acetobutylicum* ATCC 824 Reside on a Large Plasmid Whose Loss Leads to Degeneration of the Strain, Journal of Bacteriology, 1997, vol. 179:5442-5447.

David R. Woods, The Genetic Engineering of Microbial Solvent Production, Elsevier Science, 1995, vol. 13:259-264.

\* cited by examiner

SEQUENCE LISTING

<160> NUMBER OF SEQ ID NOS: 44

<210> SEQ ID NO 1
<211> LENGTH: 1179
<212> TYPE: DNA
<213> ORGANISM: Clostridium acetobutylicum

<400> SEQUENCE: 1

```
atgaaagaag ttgtaatagc tagtgcagta agaacagcga ttggatctta tggaaagtct      60
cttaaggatg taccagcagt agatttagga gctacagcta taaaggaagc agttaaaaaa     120
gcaggaataa aaccagagga tgttaatgaa gtcattttag gaaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa atgtctaga      360
gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaagctga agaagctata aaatcaggtc aatttaaaga tgaaatagtt     600
cctgtagtaa ttaaaggcag aaagggagaa actgtagttg atacagatga gcaccctaga     660
tttggatcaa ctatagaagg acttgcaaaa ttaaaacctg ccttcaaaaa agatggaaca     720
gttacagctg gtaatgcatc aggattaaat gactgtgcag cagtacttgt aatcatgagt     780
gcagaaaaag ctaagagct tggagtaaaa ccacttgcta agatagtttc ttatggttca     840
gcaggagttg acccagcaat aatgggatat ggaccttct atgcaacaaa agcagctatt     900
gaaaaagcag gttggacagt tgatgaatta gatttaatag aatcaaatga agcttttgca     960
gctcaaagtt tagcagtagc aaagatttta aatttgata tgaataaagt aaatgtaaat    1020
ggaggagcta ttgcccttgg tcatccaatt ggagcatcag gtgcaagaat actcgttact    1080
cttgtacacg caatgcaaaa aagagatgca aaaaaggct tagcaacttt atgtataggt    1140
ggcggacaag gaacagcaat attgctagaa aagtgctag                            1179
```

<210> SEQ ID NO 2
<211> LENGTH: 392
<212> TYPE: PRT
<213> ORGANISM: Clostridium acetobutylicum

<400> SEQUENCE: 2

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
```

```
                    100                 105                 110
Gly Gly Met Glu Asn Met Ser Arg Ala Pro Tyr Leu Ala Asn Asn Ala
            115                 120                 125

Arg Trp Gly Tyr Arg Met Gly Asn Ala Lys Phe Val Asp Glu Met Ile
        130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca         60
ttaaaggatg tacctgcaac agagttagga gctatagtaa taaggaagc tgtaagaaga        120 gctaatataa atccaaatga gattaatgaa gttattttg gaaatgtact tcaagctgga        180
ttaggccaaa acccagcaag acaagcagca gtaaaagcag gattaccttt agaaacacct      240
gcgtttacaa tcaataaggt tgtgggttca ggtttaagat ctataagttt agcagctcaa      300
attataaaag ctggagatgc tgataccatt gtagtaggtg gtatggaaaa tatgtctaga      360
tcaccatatt tgattaacaa tcagagatgg ggtcaaagaa tgggagatag tgaattagtt      420
gatgaaatga taaaggatgg tttgtgggat gcatttaatg atatcatat gggagtaact      480
```

```
gcagaaaata ttgcagaaca atggaatata acaagagaag agcaagatga attttcactt    540
atgtcacaac aaaaagctga aaaagccatt aaaaatggag aatttaagga tgaaatagtt    600
cctgtattaa taaagactaa aaaaggtgaa atagtctttg atcaagatga atttcctaga    660
ttcggaaaca ctattgaagc attaagaaaa cttaaaccta ttttcaagga aaatggtact    720
gttacagcag gtaatgcatc cggattaaat gatggagctg cagcactagt aataatgagc    780
gctgataaag ctaacgctct cggaataaaa ccacttgcta agattacttc ttacggatca    840
tatggggtag atccatcaat aatgggatat ggagcttttt atgcaactaa agctgcctta    900
gataaaatta atttaaaacc tgaagactta gatttaattg aagctaacga ggcatatgct    960
tctcaaagta tagcagtaac tagagattta aatttagata tgagtaaagt taatgttaat   1020
ggtggagcta tagcacttgg acatccaata ggtgcatctg gtgcacgtat tttagtaaca   1080
ttactatacg ctatgcaaaa aagagattca aaaaaaggtc ttgctactct atgtattggt   1140
ggaggtcagg gaacagctct cgtagttgaa agagactaa                           1179
```

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
                20                  25                  30

Val Ile Lys Glu Ala Val Arg Arg Ala Asn Ile Asn Pro Asn Glu Ile
            35                  40                  45

Asn Glu Val Ile Phe Gly Asn Val Leu Gln Ala Gly Leu Gly Gln Asn
        50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
                100                 105                 110

Gly Gly Met Glu Asn Met Ser Arg Ser Pro Tyr Leu Ile Asn Asn Gln
            115                 120                 125

Arg Trp Gly Gln Arg Met Gly Asp Ser Glu Leu Val Asp Glu Met Ile
        130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
```

```
                    245                 250                 255
Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390

<210> SEQ ID NO 5
<211> LENGTH: 849
<212> TYPE: DNA
<213> ORGANISM: Clostridium acetobutylicum

<400> SEQUENCE: 5
atgaaaaagg tatgtgttat aggtgcaggt actatgggtt caggaattgc tcaggcattt      60
gcagctaaag gatttgaagt agtattaaga gatattaaag atgaatttgt tgatagagga     120
ttagatttta tcaataaaaa tctttctaaa ttagttaaaa aggaaagat agaagaagct      180 actaaagttg aaatcttaac tagaatttcc ggaacagttg accttaatat ggcagctgat     240
tgcgatttag ttatagaagc agctgttgaa agaatggata ttaaaaagca gattttgct      300 gacttagaca atatatgcaa gccagaaaca attcttgcat caaatacatc atcactttca     360
ataacagaag tggcatcagc aactaaaaga cctgataagg ttataggtat gcatttcttt     420
aatccagctc ctgttatgaa gcttgtagag gtaataagag aatagctac atcacaagaa     480 acttttgatg cagttaaaga gacatctata gcaataggaa aagatcctgt agaagtagca     540
gaagcaccag gatttgttgt aaatagaata ttaataccaa tgattaatga agcagttggt     600
atattagcag aaggaatagc ttcagtagaa gacatagata aagctatgaa acttggagct     660
aatcacccaa tgggaccatt agaattaggt gattttatag tcttgatat atgtcttgct      720 ataatggatg ttttatactc agaaactgga gattctaagt atagaccaca tacattactt     780
aagaagtatg taagagcagg atggcttgga agaaaatcag gaaaggttt ctacgattat      840 tcaaaataa                                                             849

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
```

-continued

```
                        20                  25                  30

Lys Asp Glu Phe Val Asp Arg Gly Leu Asp Phe Ile Asn Lys Asn Leu
         35                  40                  45

Ser Lys Leu Val Lys Lys Gly Lys Ile Glu Glu Ala Thr Lys Val Glu
 50                  55                  60

Ile Leu Thr Arg Ile Ser Gly Thr Val Asp Leu Asn Met Ala Ala Asp
 65                  70                  75                  80

Cys Asp Leu Val Ile Glu Ala Ala Val Glu Arg Met Asp Ile Lys Lys
                 85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
            115                 120                 125

Lys Arg Pro Asp Lys Val Ile Gly Met His Phe Phe Asn Pro Ala Pro
        130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280
```

<210> SEQ ID NO 7
<211> LENGTH: 786
<212> TYPE: DNA
<213> ORGANISM: Clostridium acetobutylicum

<400> SEQUENCE: 7

```
atggaactaa acaatgtcat ccttgaaaag gaaggtaaag ttgctgtagt taccattaac    60
agacctaaag cattaaatgc gttaaatagt gatacactaa agaaatgga ttatgttata    120
ggtgaaattg aaaatgatag cgaagtactt gcagtaattt taactggagc aggagaaaaa    180
tcatttgtag caggagcaga tatttctgag atgaaggaaa tgaataccat gaaggtaga    240
aaattcggga tacttggaaa taaagtgttt agaagattag aacttcttga aaagcctgta    300
atagcagctg ttaatggttt tgctttagga ggcggatgcg aaatagctat gtcttgtgat    360
ataagaatag cttcaagcaa cgcaagattt ggtcaaccag aagtaggtct cggaataaca    420
cctggttttg gtggtacaca aagactttca gattagttg gaatgggcat ggcaaagcag    480
cttatattta ctgcacaaaa tataaaggca gatgaagcat taagaatcgg acttgtaaat    540
aaggtagtag aacctagtga attaatgaat acagcaaaag aaattgcaaa caaaattgtg    600
agcaatgctc cagtagctgt taagttaagc aaacaggcta ttaatagagg aatgcagtgt    660
```

```
gatattgata ctgctttagc atttgaatca gaagcatttg gagaatgctt ttcaacagag      720
gatcaaaagg atgcaatgac agctttcata gagaaaagaa aaattgaagg cttcaaaaat      780
agatag                                                                  786
```

<210> SEQ ID NO 8
<211> LENGTH: 261
<212> TYPE: PRT
<213> ORGANISM: Clostridium acetobutylicum

<400> SEQUENCE: 8

```
Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260
```

<210> SEQ ID NO 9
<211> LENGTH: 1197
<212> TYPE: DNA
<213> ORGANISM: Clostridium acetobutylicum

<400> SEQUENCE: 9

```
atgatagtaa aagcaaagtt tgtaaaagga tttatcagag atgtacatcc ttatggttgc      60
agaagggaag tactaaatca aatagattat tgtaagaagg ctattgggtt taggggacca     120
aagaaggttt taattgttgg agcctcatct gggtttggtc ttgctactag aatttcagtt     180
```

-continued

```
gcatttggag gtccagaagc tcacacaatt ggagtatcct atgaaacagg agctacagat    240
agaagaatag gaacagcggg atggtataat aacatatttt ttaaagaatt tgctaaaaaa    300
aaaggattag ttgcaaaaaa cttcattgag gatgcctttt ctaatgaaac caaagataaa    360
gttattaagt atataaagga tgaatttggt aaaatagatt tatttgttta gtttagct     420 gcgcctagga gaaaggacta taaaactgga aatgtttata cttcaagaat aaaaacaatt    480
ttaggagatt ttgagggacc gactattgat gttgaaagag acgagattac tttaaaaaag    540
gttagtagtg ctagcattga agaaattgaa gaaactagaa aggtaatggg tggagaggat    600
tggcaagagt ggtgtgaaga gctgctttat gaagattgtt tttcggataa agcaactacc    660
atagcatact cgtatatagg atccccaaga acctacaaga tatatagaga aggtactata    720
ggaatagcta aaaaggatct tgaagataag gctaagctta taaatgaaaa acttaacaga    780
gttataggtg gtagagcctt tgtgtctgtg aataaagcat tagttacaaa agcaagtgca    840
tatattccaa ctttttcctct ttatgcagct atttttatata aggtcatgaa agaaaaaaat    900
attcatgaaa attgtattat gcaaattgag agaatgtttt ctgaaaaaat atattcaaat    960
gaaaaaatac aatttgatga caagggaaga ttaaggatgg acgatttaga gcttagaaaa   1020
gacgttcaag acgaagttga tagaatatgg agtaatatta ctcctgaaaa ttttaaggaa   1080
ttatctgatt ataagggata caaaaaagaa ttcatgaact aaacggtttt tgatctagat   1140
ggggttgatt atagtaaaga cctggatata gaattattaa gaaaattaga acctaa       1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190
```

-continued

```
Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395

<210> SEQ ID NO 11
<211> LENGTH: 1407
<212> TYPE: DNA
<213> ORGANISM: Clostridium beijerinckii
<400> SEQUENCE: 11
atgaataaag acacactaat acctacaact aaagatttaa aagtaaaaac aaatggtgaa      60
aacattaatt taaagaacta caaggataat tcttcatgtt tcggagtatt cgaaaatgtt     120
gaaaatgcta taagcagcgc tgtacacgca caaaagatat tatcccttca ttatacaaaa     180
gagcaaagag aaaaaatcat aactgagata agaaaggccg cattacaaaa taaagaggtc     240
ttggctacaa tgattctaga agaaacacat atgggaagat atgaggataa aatattaaaa     300
catgaattgg tagctaaata tactcctggt acagaagatt taactactac tgcttggtca     360
ggtgataatg gtcttacagt tgtagaaatg tctccatatg gtgttatagg tgcaataact     420
ccttctacga atccaactga aactgtaata tgtaatagca taggcatgat agctgctgga     480
aatgctgtag tatttaacgg acacccatgc gctaaaaaat gtgttgcctt tgctgttgaa     540
atgataaata aggcaattat ttcatgtggc ggtcctgaaa atctagtaac aactataaaa     600
aatccaacta tggagtctct agatgcaatt attaagcatc cttcaataaa acttctttgc     660
ggaactgggg gtccaggaat ggtaaaaacc ctcttaaatt ctggtaagaa agctataggt     720
gctggtgctg gaaatccacc agttattgta gatgatactg ctgatataga aaaggctggt     780
aggagcatca ttgaaggctg ttcttttgat aataatttac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaaataat     960

-continued

```
gaaactcaag aatactttat aaacaaaaaa tgggtaggaa aagatgcaaa attattctta    1020
gatgaaatag atgttgagtc tccttcaaat gttaaatgca aatctgcga agtaaatgca    1080 aatcatccat tgttatgac agaactcatg atgccaatat tgccaattgt aagagttaaa    1140
gatatagatg aagctattaa atatgcaaag atagcagaac aaaatagaaa acatagtgcc    1200
tatatttatt ctaaaaatat agacaaccta aatagatttg aaagagaaat agatactact    1260 attttttgtaa agaatgctaa atcttttgct ggtgttggtt atgaagcaga aggatttaca    1320
actttcacta ttgctggatc tactggtgag ggaataaccct ctgcaaggaa ttttacaaga    1380
caaagaagat gtgtacttgc cggctaa                                      1407
```

<210> SEQ ID NO 12
<211> LENGTH: 468
<212> TYPE: PRT
<213> ORGANISM: Clostridium beijerinckii

<400> SEQUENCE: 12

```
Met Asn Lys Asp Thr Leu Ile Pro Thr Thr Lys Asp Leu Lys Val Lys
 1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
```

```
                290              295              300
Glu Asp Gln Val Ser Lys Leu Ile Asp Leu Val Leu Gln Lys Asn Asn
305                 310              315                  320

Glu Thr Gln Glu Tyr Phe Ile Asn Lys Lys Trp Val Gly Lys Asp Ala
                325              330                  335

Lys Leu Phe Leu Asp Glu Ile Asp Val Glu Ser Pro Ser Asn Val Lys
                340              345              350

Cys Ile Ile Cys Glu Val Asn Ala Asn His Pro Phe Val Met Thr Glu
                355              360              365

Leu Met Met Pro Ile Leu Pro Ile Val Arg Val Lys Asp Ile Asp Glu
370                 375              380

Ala Ile Lys Tyr Ala Lys Ile Ala Glu Gln Asn Arg Lys His Ser Ala
385                 390              395                  400

Tyr Ile Tyr Ser Lys Asn Ile Asp Asn Leu Asn Arg Phe Glu Arg Glu
                405              410              415

Ile Asp Thr Thr Ile Phe Val Lys Asn Ala Lys Ser Phe Ala Gly Val
                420              425              430

Gly Tyr Glu Ala Glu Gly Phe Thr Thr Phe Thr Ile Ala Gly Ser Thr
                435              440              445

Gly Glu Gly Ile Thr Ser Ala Arg Asn Phe Thr Arg Gln Arg Arg Cys
450                 455              460

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt tcgaatattc aataccaact agaattttt tcggtaaaga taagataaat     60
gtacttggaa gagagcttaa aaaatatggt tctaaagtgc ttatagttta tggtggagga    120
agtataaaga gaaatggaat atatgataaa gctgtaagta tacttgaaaa aacagtatt    180 aaattttatg aacttgcagg agtagagcca atccaagag taactacagt tgaaaaagga    240
gttaaaatat gtagagaaaa tggagttgaa gtagtactag ctataggtgg aggaagtgca    300
atagattgcg caaaggttat agcagcagca tgtgaatatg atggaaatcc atgggatatt    360
gtgttagatg gctcaaaaat aaaaagggtg cttcctatag ctgtatatt aaccattgct    420 gcaacaggat cagaaatgga tacgtgggca gtaataaata tatggatac aaacgaaaaa    480 ctaattgcgg cacatccaga tatggctcct aagttttcta tattagatcc aacgtatacg    540
tataccgtac ctaccaatca aacagcagca ggaacagctg atattatgag tcatatattt    600
gaggtgtatt ttagtaatac aaaaacagca tatttgcagg atagaatggc agaagcgtta    660
ttaagaactt gtattaaata tggaggaata gctcttgaga agccggatga ttatgaggca    720
agagccaatc taatgtgggc ttcaagtctt gcgataaatg acttttaac atatggtaaa    780 gacactaatt ggagtgtaca cttaatggaa catgaattaa gtgcttatta cgacataaca    840
cacggcgtag gcttgcaat tttaaccct aattggatgg agtatatttt aaataatgat    900
acagtgtaca gtttgttga atatggtgta atgtttggg aatagacaa agaaaaaaat    960 cactatgaca tagcacatca agcaatacaa aaaacaagag attactttgt aaatgtacta   1020
ggtttaccat ctagactgag agatgttgga attgaagaag aaaaattgga cataatggca   1080
```

-continued

```
aaggaatcag taaagcttac aggaggaacc ataggaaacc taagaccagt aaacgcctcc   1140
gaagtcctac aaatattcaa aaatctgtg taaaacgcct ccgaagtcct acaaatattc    1200
aaaaaatctg tgtaa                                                    1215
```

<210> SEQ ID NO 14
<211> LENGTH: 390
<212> TYPE: PRT
<213> ORGANISM: Clostridium acetobutylicum

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95

Gly Gly Ser Ala Ile Asp Cys Ala Lys Val Ile Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350
```

Glu Glu Lys Leu Asp Ile Met Ala Lys Glu Ser Val Lys Leu Thr Gly
            355                 360                 365

Gly Thr Ile Gly Asn Leu Arg Pro Val Asn Ala Ser Glu Val Leu Gln
        370                 375                 380

Ile Phe Lys Lys Ser Val
385                 390

<210> SEQ ID NO 15
<211> LENGTH: 1170
<212> TYPE: DNA
<213> ORGANISM: Clostridium acetobutylicum

<400> SEQUENCE: 15
atgctaagtt ttgattattc aataccaact aaagtttttt ttggaaaagg aaaaatagac      60
gtaattggag aagaaattaa gaaatatggc tcaagagtgc ttatagttta tggcggagga     120
agtataaaaa ggaacggtat atatgataga gcaacagcta tattaaaaga aacaatata     180 gctttctatg aactttcagg agtagagcca atcctagga taacaacagt aaaaaaaggc      240
atagaaatat gtagagaaaa taatgtggat ttagtattag caatagggg aggaagtgca      300 atagactgtt ctaaggtaat tgcagctgga gtttattatg atggcgatac atgggacatg     360
gttaaagatc catctaaaat aactaaagtt cttccaattg caagtatact tactctttca     420
gcaacagggt ctgaaatgga tcaaattgca gtaatttcaa atatggagac taatgaaaag     480
cttggagtag acatgatga tatgagacct aaattttcag tgttagatcc tacatatact     540
tttacagtac ctaaaaatca aacagcagcg ggaacagctg acattatgag tcacaccttt     600
gaatcttact ttagtggtgt tgaaggtgct tatgtgcagg acggtatagc agaagcaatc     660
ttaagaacat gtataaagta tggaaaaata gcaatggaga agactgatga ttacgaggct     720
agagctaatt tgatgtgggc ttcaagttta gctataaatg gtctattatc acttggtaag     780
gatagaaaat ggagttgtca tcctatggaa cacgagttaa gtgcatatta tgatataaca     840
catggtgtag acttgcaat tttaacacct aattggatgg aatatattct aaatgacgat     900
acacttcata atttgtttc ttatggaata aatgtttggg aatagacaa gaacaaagat     960 aactatgaaa tagcacgaga ggctattaaa aatacgagag aatactttaa ttcattgggt    1020
attccttcaa agcttagaga agttggaata ggaaaagata aactagaact aatggcaaag    1080
caagctgtta gaaattctgg aggaacaata ggaagtttaa gaccaataaa tgcagaggat    1140
gttcttgaga tatttaaaaa atcttattaa                                     1170

<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly

```
                65                  70                  75                  80
        Ile Glu Ile Cys Arg Glu Asn Asn Val Asp Leu Val Leu Ala Ile Gly
                        85                  90                  95

Gly Gly Ser Ala Ile Asp Cys Ser Lys Val Ile Ala Ala Gly Val Tyr
                        100                 105                 110

Tyr Asp Gly Asp Thr Trp Asp Met Val Lys Asp Pro Ser Lys Ile Thr
                        115                 120                 125

Lys Val Leu Pro Ile Ala Ser Ile Leu Thr Leu Ser Ala Thr Gly Ser
                130                 135                 140

Glu Met Asp Gln Ile Ala Val Ile Ser Asn Met Glu Thr Asn Glu Lys
        145                 150                 155                 160

Leu Gly Val Gly His Asp Asp Met Arg Pro Lys Phe Ser Val Leu Asp
                        165                 170                 175

Pro Thr Tyr Thr Phe Thr Val Pro Lys Asn Gln Thr Ala Ala Gly Thr
                        180                 185                 190

Ala Asp Ile Met Ser His Thr Phe Glu Ser Tyr Phe Ser Gly Val Glu
                        195                 200                 205

Gly Ala Tyr Val Gln Asp Gly Ile Ala Glu Ala Ile Leu Arg Thr Cys
                210                 215                 220

Ile Lys Tyr Gly Lys Ile Ala Met Glu Lys Thr Asp Asp Tyr Glu Ala
        225                 230                 235                 240

Arg Ala Asn Leu Met Trp Ala Ser Ser Leu Ala Ile Asn Gly Leu Leu
                        245                 250                 255

Ser Leu Gly Lys Asp Arg Lys Trp Ser Cys His Pro Met Glu His Glu
                        260                 265                 270

Leu Ser Ala Tyr Tyr Asp Ile Thr His Gly Val Gly Leu Ala Ile Leu
                        275                 280                 285

Thr Pro Asn Trp Met Glu Tyr Ile Leu Asn Asp Asp Thr Leu His Lys
                290                 295                 300

Phe Val Ser Tyr Gly Ile Asn Val Trp Gly Ile Asp Lys Asn Lys Asp
        305                 310                 315                 320

Asn Tyr Glu Ile Ala Arg Glu Ala Ile Lys Asn Thr Arg Glu Tyr Phe
                        325                 330                 335

Asn Ser Leu Gly Ile Pro Ser Lys Leu Arg Glu Val Gly Ile Gly Lys
                        340                 345                 350

Asp Lys Leu Glu Leu Met Ala Lys Gln Ala Val Arg Asn Ser Gly Gly
                        355                 360                 365

Thr Ile Gly Ser Leu Arg Pro Ile Asn Ala Glu Asp Val Leu Glu Ile
                370                 375                 380

Phe Lys Lys Ser Tyr
        385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc     180 ggcacctta atgagctgga cggggagctg atcgccttca gcagtcaggt ctatcagctg     240
cgcgccgacg gcagcgcgcg caaagcccag ccggagcaga aaacgccgtt cgcggtgatg     300
```

```
acctggttcc agccgcagta ccggaaaacc tttgaccatc cggtgagccg ccagcagctg      360
cacgaggtga tcgaccagca aatcccctct gacaacctgt tctgcgccct gcgcatcgac      420
ggccatttcc gccatgccca tacccgcacc gtgccgcgcc agacgccgcc gtaccgggcg      480
atgaccgacg tcctcgacga tcagccggtg ttccgcttta accagcgcga aggggtgctg      540
gtcggcttcc ggaccccgca gcatatgcag gggatcaacg tcgccgggta tcacgagcac      600
tttattaccg atgaccgcaa aggcggcggt cacctgctgg attaccagct cgaccatggg      660
gtgctgacct tcggcgaaat tcacaagctg atgatcgacc tgcccgccga cagcgcgttc      720
ctgcaggcta atctgcatcc cgataatctc gatgccgcca tccgttccgt agaaagttaa      780
```

<210> SEQ ID NO 18
<211> LENGTH: 259
<212> TYPE: PRT
<213> ORGANISM: Klebsiella pneumoniae

<400> SEQUENCE: 18

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA

<213> ORGANISM: Klebsiella pneumoniae

<400> SEQUENCE: 19

```
atggacaaac agtatccggt acgccagtgg gcgcacggcg ccgatctcgt cgtcagtcag    60
ctggaagctc agggagtacg ccaggtgttc ggcatcccg gcgccaaaat tgacaaggtc   120
ttcgactcac tgctggattc ctcgattcgc attattccgg tacgccacga agccaacgcc   180
gcgtttatgg ccgccgccgt cggacgcatt accggcaaag cgggcgtggc gctggtcacc   240
tccggtccgg gctgttccaa cctgatcacc ggcatggcca ccgcgaacag cgaaggcgac   300
ccggtggtgg ccctgggcgg cgcggtaaaa cgcgccgata agcgaagca ggtccaccag   360
agtatggata cggtggcgat gttcagcccg gtcaccaaat acgccgtcga ggtgacggcg   420
ccggatgcgc tggcggaagt ggtctccaac gccttccgcg ccgccgagca gggccggccg   480
ggcagcgcgt tcgttagcct gccgcaggat gtggtcgatg cccggtcag cggcaaagtg   540
ctgccggcca gcggggcccc gcagatgggc ccgcgccgg atgatgccat cgaccaggtg   600
gcgaagctta tcgcccaggc gaagaacccg atcttcctgc tcggcctgat ggccagccag   660
ccggaaaaca gcaaggcgct cgccgtttg ctggagacca ccatattcc agtcaccagc   720
acctatcagg ccgccggagc ggtgaatcag gataacttct ctcgcttcgc cggccgggtt   780
gggctgttta caaccaggc cggggaccgt ctgctgcagc tcgccgacct ggtgatctgc   840
atcggctaca gcccggtgga atacgaaccg gcgatgtgga acagcggcaa cgcgacgctg   900
gtgcacatcg acgtgctgcc cgcctatgaa gagcgcaact acaccccgga tgtcgagctg   960
gtgggcgata tcgccggcac tctcaacaag ctggcgcaaa atatcgatca tcggctggtg  1020
ctctccccgc aggcggcgga gatcctccgc gaccgccagc accagcgcga gctgctggac  1080
cgccgcggcg cgcagctgaa ccagtttgcc ctgcatccgc tgcgcatcgt tcgcgccatg  1140
caggacatcg tcaacagcga cgtcacgttg accgtggaca tgggcagctt ccatatctgg  1200
attgcccgct acctgtacag cttccgcgcc cgtcaggtga tgatctccaa cggccagcag  1260
accatgggcg tcgccctgcc ctgggctatc ggcgcctggc tggtcaatcc tgagcgaaaa  1320
gtggtctccg tctccggcga cggcggcttc ctgcagtcga gcatggagct ggagaccgcc  1380
gtccgcctga agccaacgt actgcacctg atctgggtcg ataacggcta caacatggtg  1440
gccattcagg aagagaaaaa ataccagcgc ctgtccggcg tcgagttcgg gccgatggat  1500
tttaaagcct atgccgaatc cttcggcgcg aaagggtttg ccgtggaaag cgccgaggcg  1560
ctggagccga ccctgcacgc ggcgatggac gtcgacggcc cggcggtggt ggccattccg  1620
gtggattatc gcgataaccc gctgctgatg ggccagctgc atctgagtca gattctgtaa  1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60
```

```
Ala Ala Val Gly Arg Ile Thr Gly Lys Ala Gly Val Ala Leu Val Thr
 65                  70                  75                  80

Ser Gly Pro Gly Cys Ser Asn Leu Ile Thr Gly Met Ala Thr Ala Asn
                 85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
            115                 120                 125

Ser Pro Val Thr Lys Tyr Ala Val Glu Val Thr Ala Pro Asp Ala Leu
        130                 135                 140

Ala Glu Val Val Ser Asn Ala Phe Arg Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
            195                 200                 205

Asn Pro Ile Phe Leu Leu Gly Leu Met Ala Ser Gln Pro Glu Asn Ser
210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
450                 455                 460

Ala Asn Val Leu His Leu Ile Trp Val Asp Asn Gly Tyr Asn Met Val
465                 470                 475                 480
```

Ala Ile Gln Glu Glu Lys Lys Tyr Gln Arg Leu Ser Gly Val Glu Phe
            485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
            515                 520                 525

Met Asp Val Asp Gly Pro Ala Val Val Ala Ile Pro Val Asp Tyr Arg
            530                 535                 540

Asp Asn Pro Leu Leu Met Gly Gln Leu His Leu Ser Gln Ile Leu
545                 550                 555

<210> SEQ ID NO 21
<211> LENGTH: 771
<212> TYPE: DNA
<213> ORGANISM: Klebsiella pneumoniae

<400> SEQUENCE: 21
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt aacaggcgc gcaaaacgct gggcggcttc      240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc ctgttcccag     420
gccggccacg tcggcaaccc ggagctggcg gtgtatagct ccagtaaatt cgcggtacgc     480
ggcttaaccc agaccgccgc tcgcgacctc gcgccgctgg catcacggt caacggctac      540 tgcccgggga ttgtcaaaac gccaatgtgg gccgaaattg accgccaggt gtccgaagcc     600
gccggtaaac cgctgggcta cggtaccgcc gagttcgcca aacgcatcac tctcggtcgt     660
ctgtccgagc cggaagatgt cgccgcctgc gtctcctatc ttgccagccc ggattctgat     720
tacatgaccg tcagtcgtt gctgatcgac ggcgggatgg tatttaacta a               771

<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
            35                  40                  45

Ala Gly Gly His Ala Val Ala Val Lys Val Asp Val Ser Asp Arg Asp
        50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
            85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu

```
                    115                 120                 125
Gly His Gly Gly Lys Ile Ile Asn Ala Cys Ser Gln Ala Gly His Val
        130                 135                 140

Gly Asn Pro Glu Leu Ala Val Tyr Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Met Val Phe Asn
                245                 250                 255

<210> SEQ ID NO 23
<211> LENGTH: 1665
<212> TYPE: DNA
<213> ORGANISM: Klebsiella oxytoca

<400> SEQUENCE: 23
atgagatcga aaagatttga agcactggcg aaacgccctg tgaatcagga cggcttcgtt    60
aaggagtgga tcgaagaagg ctttatcgcg atggaaagcc cgaacgaccc aaaaccgtcg   120
attaaaatcg ttaacggcgc ggtgaccgag ctggacggga accggtaagc gattttgac    180
ctgatcgacc actttatcgc cgctacggt atcaacctga accgcgccga agaagtgatg    240
gcgatggatt cggtcaagct ggccaacatg ctgtgcgatc cgaacgttaa acgcagcgaa   300
atcgtcccgc tgaccaccgc gatgacgccg gcgaaaattg tcgaagtggt ttcgcatatg   360
aacgtcgtcg agatgatgat ggcgatgcag aaaatgcgcg cccgccgcac cccgtcccag   420
caggcgcacg tcaccaacgt caaagataac ccggtacaga ttgccgccga cgccgccgaa   480
ggggcatggc gcggatttga cgaacaggaa accaccgttg cggtagcgcg ctatgcgccg   540
ttcaacgcca tcgcgctgct ggtgggctcg caggtaggcc gtccgggcgt gctgacgcag   600
tgctcgctgg aagaagccac cgagctgaag ctcggcatgc tgggccacac ctgctacgcc   660
gaaaccatct ccgtctacgg caccgagccg gtctttaccg acgcgacga cacgccgtgg   720
tcgaagggct cctcgcctc gtcctacgcc tctcgcgggc tgaaaatgcg ctttacctcc   780
ggctccggct cggaagtgca gatgggctac gccgaaggca atccatgct ttatctggaa   840
gcgcgctgca tctacatcac caaagccgcg gcgtacagg tctgcaaaa cggttccgta    900
agctgcatcg gcgtgccgtc tgcggtgcct ccggcattc gcgcggtgct ggcggaaaac   960
ctgatctgtt cgtcgctgga tctggagtgc gcctccagca acgaccagac cttcacccac  1020
tccgatatgc gtcgtaccgc gcgcctgctg atgcagttcc tgccgggcac cgactttatc  1080
tcctccggtt attccgcggt gccgaactac gacaacatgt cgccggctc aacgaagat   1140
gccgaagact tgacgactac aacgtcatc cagcgcgacc tgaaggtgga cggcggtttg  1200
cgtccggttc gcgaagagga cgtcatcgcc atccgtaaca agccgcccg cgcgctgcag  1260
gccgtgtttg ccggaatggg gctgccgccg attaccgatg aagaagttga agccgcgacc  1320
tacgcccacg gttcgaaaga tatgccggag cgcaacatcg tcgaagacat caagttcgcc  1380
```

-continued

```
caggaaatca tcaataaaaa ccgcaacggt ctggaagtgg tgaaagcgct ggcgcagggc    1440
ggattcaccg acgtggccca ggacatgctc aacatccaga aagctaagct gaccggggac    1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                    1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320
```

Leu Ile Cys Ser Ser Leu Asp Leu Glu Cys Ala Ser Asn Asp Gln
            325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
            355                 360                 365

Asn Tyr Asp Asn Met Phe Ala Gly Ser Asn Glu Asp Ala Glu Asp Phe
        370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
            435                 440                 445

Pro Glu Arg Asn Ile Val Glu Asp Ile Lys Phe Ala Gln Glu Ile Ile
        450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
            515                 520                 525

Thr Gly Tyr Arg Leu Gln Gly Glu Arg Trp Glu Glu Ile Lys Asn Ile
        530                 535                 540

Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
atggaaatta tgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg gcgacggctt cctgacggaa gtgggcgaag cgcgtcaggg aacccagcag     180
gacgaagtga ttatcgccgt cggcccggct ttcggcctgg cgcagaccgt caatatcgtc     240
ggcatcccgc ataagagcat tttgcgcgaa gtcattgccg gtattgaaga agaaggcatt     300
aaggcgcgcg tgattcgctg ctttaaatcc tccgacgtgg ccttcgtcgc cgttgaaggt     360
aatcgcctga gcggctccgg catctctatc ggcatccagt cgaaaggcac cacggtgatc     420
caccagcagg ggctgccgcc gctctctaac ctggagctgt tcccgcaggc gccgctgctg     480
accctggaaa cctatcgcca gatcggcaaa aacgccgccc gctatgcgaa cgcgaatcg      540 ccgcagccgg tcccgacgct gaatgaccag atggcgcggc cgaagtacca ggcgaaatcg     600
gccattttgc acattaaaga gaccaagtac gtggtgacgg caaaaaccc gcaggaactg      660 cgcgtggcgc tttga                                                     675

<210> SEQ ID NO 26

<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc cgctggcgaa caagcacccg gaatgggtga aaaccgccac caataaaacg     180
ctggacgact ttacgctgga aaacgtgctg agcaataaag tcaccgccca ggatatgcgt     240
attaccccgg aaaccctgcg cttacaggct tctattgcca agacgcgggg ccgcgaccgg     300
ctggcgatga acttcgagcg cgccgccgag ctgaccgcgg taccggacga tcgcattctt     360
gaaatctaca cgccctccg ccctatcgc tcgacgaaag aggagctgct ggcgatcgcc     420
gacgatctcg aaagccgcta tcaggcgaag atttgcgccg ctttcgttcg cgaagcggcc     480
acgctgtacg tcgagcgtaa aaaactcaaa ggcgacgatt aa                       522

<210> SEQ ID NO 28
<211> LENGTH: 173
<212> TYPE: PRT
<213> ORGANISM: Klebsiella oxytoca

<400> SEQUENCE: 28

```
Met Asn Thr Asp Ala Ile Glu Ser Met Val Arg Asp Val Leu Ser Arg
1               5                   10                  15
Met Asn Ser Leu Gln Gly Glu Ala Pro Ala Ala Pro Ala Ala Gly
            20                  25                  30
Gly Ala Ser Arg Ser Ala Arg Val Ser Asp Tyr Pro Leu Ala Asn Lys
        35                  40                  45
His Pro Glu Trp Val Lys Thr Ala Thr Asn Lys Thr Leu Asp Asp Phe
    50                  55                  60
Thr Leu Glu Asn Val Leu Ser Asn Lys Val Thr Ala Gln Asp Met Arg
65                  70                  75                  80
Ile Thr Pro Glu Thr Leu Arg Leu Gln Ala Ser Ile Ala Lys Asp Ala
                85                  90                  95
Gly Arg Asp Arg Leu Ala Met Asn Phe Glu Arg Ala Ala Glu Leu Thr
            100                 105                 110
Ala Val Pro Asp Asp Arg Ile Leu Glu Ile Tyr Asn Ala Leu Arg Pro
        115                 120                 125
Tyr Arg Ser Thr Lys Glu Glu Leu Leu Ala Ile Ala Asp Asp Leu Glu
    130                 135                 140
Ser Arg Tyr Gln Ala Lys Ile Cys Ala Ala Phe Val Arg Glu Ala Ala
145                 150                 155                 160
Thr Leu Tyr Val Glu Arg Lys Lys Leu Lys Gly Asp Asp
                165                 170
```

<210> SEQ ID NO 29
<211> LENGTH: 1041
<212> TYPE: DNA
<213> ORGANISM: Rhodococcus ruber

<400> SEQUENCE: 29

```
atgaaagccc tccagtacac cgagatcggc tccgagccgg tcgtcgtcga cgtccccacc      60
ccggcgcccg gccgggtga gatcctgctg aaggtcaccg cggccggctt gtgccactcg     120
gacatcttcg tgatggacat gccggcagag cagtacatct acggtcttcc cctcacccct c  180
ggccacgagg gcgtcggcac cgtcgccgaa ctcggcgccg cgtcaccgg attcgagacg     240
ggggacgccg tcgccgtgta cgggccgtgg gggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg gcacgtcgg catccagatc ctgcgcgccg tcagcgcggc ccgcgtgatc     600
gccgtcgatc tcgacgacga ccgactcgcg ctcgcccgcg aggtcggcgc cgacgcggcg     660
gtgaagtcgg cgccggggc ggcggacgcg atccgggagc tgaccggcgg tgagggcgcg     720
acggcggtgt cgacttcgt cggcgcccag tcgacgatcg acacggcgca gcaggtggtc     780
gcgatcgacg ggcacatctc ggtggtcggc atccatgccg cgcccacgc caaggtcggc     840
ttcttcatga tcccgttcgg cgcgtccgtc gtgacgccgt actggggcac gcggtccgag     900
ctgatggacg tcgtggacct ggccgtgcc ggccggctcg acatccacac cgagacgttc     960
accctcgacg agggacccac ggcctaccgg cggctacgcg agggcagcat ccgcggccgc    1020
ggggtggtcg tcccgggctg a                                              1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345
```

<210> SEQ ID NO 31
<211> LENGTH: 1476
<212> TYPE: DNA

<213> ORGANISM: Escherichia coli

<400> SEQUENCE: 31

```
atggctaact acttcaatac actgaatctg cgccagcagc tggcacagct gggcaaatgt      60
cgctttatgg gccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc cgaaatgccc aggcaccgaa     480
gtgcgtgaag agtacaaacg tgggttcggc gtaccgacgc tgattgccgt tcacccggaa     540
aacgatccga aggcgaaggg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
gcgaaactgc gtgcttatgc gctttctgaa cagctgaaag atcatggc accctgttc        900
cagaaacata tggacgacat catctccggc gaattctctt ccggtatgat ggcggactgg     960
gccaacgatg ataagaaact gctgacctgg cgtgaagaga ccggcaaaac cgcgtttgaa    1020
accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tgggtaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                              1476
```

<210> SEQ ID NO 32
<211> LENGTH: 491
<212> TYPE: PRT
<213> ORGANISM: Escherichia coli

<400> SEQUENCE: 32

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Val Ile Val Gly Cys Gly Ala Gln
            35                  40                  45

Gly Leu Asn Gln Gly Leu Asn Met Arg Asp Ser Gly Leu Asp Ile Ser
        50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95
```

-continued

```
Pro Gln Ala Asp Leu Val Ile Asn Leu Thr Pro Asp Lys Gln His Ser
            100                 105                 110
Asp Val Val Arg Thr Val Gln Pro Leu Met Lys Asp Gly Ala Ala Leu
        115                 120                 125
Gly Tyr Ser His Gly Phe Asn Ile Val Glu Val Gly Glu Gln Ile Arg
    130                 135                 140
Lys Asp Ile Thr Val Val Met Val Ala Pro Lys Cys Pro Gly Thr Glu
145                 150                 155                 160
Val Arg Glu Glu Tyr Lys Arg Gly Phe Gly Val Pro Thr Leu Ile Ala
                165                 170                 175
Val His Pro Glu Asn Asp Pro Lys Gly Glu Gly Met Ala Ile Ala Lys
            180                 185                 190
Ala Trp Ala Ala Thr Gly Gly His Arg Ala Gly Val Leu Glu Ser
        195                 200                 205
Ser Phe Val Ala Glu Val Lys Ser Asp Leu Met Gly Glu Gln Thr Ile
    210                 215                 220
Leu Cys Gly Met Leu Gln Ala Gly Ser Leu Leu Cys Phe Asp Lys Leu
225                 230                 235                 240
Val Glu Glu Gly Thr Asp Pro Ala Tyr Ala Glu Lys Leu Ile Gln Phe
                245                 250                 255
Gly Trp Glu Thr Ile Thr Glu Ala Leu Lys Gln Gly Gly Ile Thr Leu
            260                 265                 270
Met Met Asp Arg Leu Ser Asn Pro Ala Lys Leu Arg Ala Tyr Ala Leu
        275                 280                 285
Ser Glu Gln Leu Lys Glu Ile Met Ala Pro Leu Phe Gln Lys His Met
    290                 295                 300
Asp Asp Ile Ile Ser Gly Glu Phe Ser Ser Gly Met Met Ala Asp Trp
305                 310                 315                 320
Ala Asn Asp Asp Lys Lys Leu Leu Thr Trp Arg Glu Glu Thr Gly Lys
                325                 330                 335
Thr Ala Phe Glu Thr Ala Pro Gln Tyr Glu Gly Lys Ile Gly Glu Gln
            340                 345                 350
Glu Tyr Phe Asp Lys Gly Val Leu Met Ile Ala Met Val Lys Ala Gly
        355                 360                 365
Val Glu Leu Ala Phe Glu Thr Met Val Asp Ser Gly Ile Ile Glu Glu
    370                 375                 380
Ser Ala Tyr Tyr Glu Ser Leu His Glu Leu Pro Leu Ile Ala Asn Thr
385                 390                 395                 400
Ile Ala Arg Lys Arg Leu Tyr Glu Met Asn Val Val Ile Ser Asp Thr
                405                 410                 415
Ala Glu Tyr Gly Asn Tyr Leu Phe Ser Tyr Ala Cys Val Pro Leu Leu
            420                 425                 430
Lys Pro Phe Met Ala Glu Leu Gln Pro Gly Asp Leu Gly Lys Ala Ile
        435                 440                 445
Pro Glu Gly Ala Val Asp Asn Gly Gln Leu Arg Asp Val Asn Glu Ala
    450                 455                 460
Ile Arg Ser His Ala Ile Glu Gln Val Gly Lys Lys Leu Arg Gly Tyr
465                 470                 475                 480
Met Thr Asp Met Lys Arg Ile Ala Val Ala Gly
                485                 490
```

<210> SEQ ID NO 33
<211> LENGTH: 1851

<212> TYPE: DNA
<213> ORGANISM: Escherichia coli

<400> SEQUENCE: 33

```
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt tcaacaccat tgcggtggat     240
gatgggattg ccatgggcca cggggggatg ctttattcac tgccatctcg cgaactgatc     300
gctgattccg ttgagtatat ggtcaacgcc cactgcgccg acgccatggt ctgcatctct     360
aactgcgaca aaatcacccc ggggatgctg atggcttccc tgcgcctgaa tattccggtg     420
atctttgttt ccggcggccc gatggaggcc gggaaaacca actttccga tcagatcatc      480
aagctcgatc tggttgatgc gatgatccag ggcgcagacc cgaaagtatc tgactcccag     540
agcgatcagg ttgaacgttc cgcgtgtccg acctgcggtt cctgctccgg atgtttacc      600
gctaactcaa tgaactgcct gaccgaagcg ctgggcctgt cgcagccggg caacggctcg     660
ctgctggcaa cccacgccga ccgtaagcag ctgttcctta tgctggtaa acgcattgtt      720
gaattgacca aacgttatta cgagcaaaac gacgaaagtg cactgccgcg taatatcgcc     780
agtaaggcgg cgtttgaaaa cgccatgacg ctggatatcg atgggtgg atcgactaac       840
accgtacttc acctgctggc ggcggcgcag aagcggaaa tcgacttcac catgagtgat      900
atcgataagc tttcccgcaa ggttccacag ctgtgtaaag ttgcgccgag cacccagaaa     960
taccatatgg aagatgttca ccgtgctggt ggtgttatcg gtattctcgg cgaactggat    1020
cgcgcggggt tactgaaccg tgatgtgaaa aacgtacttg gcctgacgtt gccgcaaacg    1080
ctggaacaat acgacgttat gctgacccag gatgacgcgg taaaaaatat gttccgcgca    1140
ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcg tgctctacgg taactttgcg gaaaacggct gcatcgtgaa acggcaggc      1320
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc tggtggcacc     1560
tctggtcttt ccatcggcca cgtctcaccg gaagcggcaa gcggcggcag cattggcctg    1620
attgaagatg tgaccctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tgggggggtta a            1851
```

<210> SEQ ID NO 34
<211> LENGTH: 616
<212> TYPE: PRT
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
```

```
                20                  25                  30
Gly Lys Pro Ile Ile Ala Val Val Asn Ser Phe Thr Gln Phe Val Pro
            35                  40                  45
Gly His Val His Leu Arg Asp Leu Gly Lys Leu Val Ala Glu Gln Ile
        50                  55                  60
Glu Ala Ala Gly Gly Val Ala Lys Glu Phe Asn Thr Ile Ala Val Asp
65                  70                  75                  80
Asp Gly Ile Ala Met Gly His Gly Gly Met Leu Tyr Ser Leu Pro Ser
                85                  90                  95
Arg Glu Leu Ile Ala Asp Ser Val Glu Tyr Met Val Asn Ala His Cys
            100                 105                 110
Ala Asp Ala Met Val Cys Ile Ser Asn Cys Asp Lys Ile Thr Pro Gly
        115                 120                 125
Met Leu Met Ala Ser Leu Arg Leu Asn Ile Pro Val Ile Phe Val Ser
130                 135                 140
Gly Gly Pro Met Glu Ala Gly Lys Thr Lys Leu Ser Asp Gln Ile Ile
145                 150                 155                 160
Lys Leu Asp Leu Val Asp Ala Met Ile Gln Gly Ala Asp Pro Lys Val
                165                 170                 175
Ser Asp Ser Gln Ser Asp Gln Val Glu Arg Ser Ala Cys Pro Thr Cys
            180                 185                 190
Gly Ser Cys Ser Gly Met Phe Thr Ala Asn Ser Met Asn Cys Leu Thr
        195                 200                 205
Glu Ala Leu Gly Leu Ser Gln Pro Gly Asn Gly Ser Leu Leu Ala Thr
210                 215                 220
His Ala Asp Arg Lys Gln Leu Phe Leu Asn Ala Gly Lys Arg Ile Val
225                 230                 235                 240
Glu Leu Thr Lys Arg Tyr Tyr Glu Gln Asn Asp Glu Ser Ala Leu Pro
                245                 250                 255
Arg Asn Ile Ala Ser Lys Ala Ala Phe Glu Asn Ala Met Thr Leu Asp
            260                 265                 270
Ile Ala Met Gly Gly Ser Thr Asn Thr Val Leu His Leu Leu Ala Ala
        275                 280                 285
Ala Gln Glu Ala Glu Ile Asp Phe Thr Met Ser Asp Ile Asp Lys Leu
290                 295                 300
Ser Arg Lys Val Pro Gln Leu Cys Lys Val Ala Pro Ser Thr Gln Lys
305                 310                 315                 320
Tyr His Met Glu Asp Val His Arg Ala Gly Gly Val Ile Gly Ile Leu
                325                 330                 335
Gly Glu Leu Asp Arg Ala Gly Leu Leu Asn Arg Asp Val Lys Asn Val
            340                 345                 350
Leu Gly Leu Thr Leu Pro Gln Thr Leu Glu Gln Tyr Asp Val Met Leu
        355                 360                 365
Thr Gln Asp Asp Ala Val Lys Asn Met Phe Arg Ala Gly Pro Ala Gly
370                 375                 380
Ile Arg Thr Thr Gln Ala Phe Ser Gln Asp Cys Arg Trp Asp Thr Leu
385                 390                 395                 400
Asp Asp Asp Arg Ala Asn Gly Cys Ile Arg Ser Leu Glu His Ala Tyr
                405                 410                 415
Ser Lys Asp Gly Gly Leu Ala Val Leu Tyr Gly Asn Phe Ala Glu Asn
            420                 425                 430
Gly Cys Ile Val Lys Thr Ala Gly Val Asp Asp Ser Ile Leu Lys Phe
        435                 440                 445
```

```
Thr Gly Pro Ala Lys Val Tyr Glu Ser Gln Asp Asp Ala Val Glu Ala
    450                 455                 460
Ile Leu Gly Gly Lys Val Val Ala Gly Asp Val Val Ile Arg Tyr
465                 470                 475                 480
Glu Gly Pro Lys Gly Pro Gly Met Gln Glu Met Leu Tyr Pro Thr
                485                 490                 495
Ser Phe Leu Lys Ser Met Gly Leu Gly Lys Ala Cys Ala Leu Ile Thr
            500                 505                 510
Asp Gly Arg Phe Ser Gly Gly Thr Ser Gly Leu Ser Ile Gly His Val
        515                 520                 525
Ser Pro Glu Ala Ala Ser Gly Gly Ser Ile Gly Leu Ile Glu Asp Gly
    530                 535                 540
Asp Leu Ile Ala Ile Asp Ile Pro Asn Arg Gly Ile Gln Leu Gln Val
545                 550                 555                 560
Ser Asp Ala Glu Leu Ala Ala Arg Arg Glu Ala Gln Asp Ala Arg Gly
                565                 570                 575
Asp Lys Ala Trp Thr Pro Lys Asn Arg Glu Arg Gln Val Ser Phe Ala
            580                 585                 590
Leu Arg Ala Tyr Ala Ser Leu Ala Thr Ser Ala Asp Lys Gly Ala Val
        595                 600                 605
Arg Asp Lys Ser Lys Leu Gly Gly
    610                 615

<210> SEQ ID NO 35
<211> LENGTH: 1662
<212> TYPE: DNA
<213> ORGANISM: Lactococcus lactis

<400> SEQUENCE: 35
tctagacata tgtatactgt gggggattac ctgctggatc gcctgcacga actggggatt      60
gaagaaattt tcggtgtgcc aggcgattat aacctgcagt tcctggacca gattatctcg     120
cacaaagata tgaagtgggt cggtaacgcc aacgaactga cgcgagcta tatggcagat      180 ggttatgccc gtaccaaaaa agctgctgcg tttctgacga cctttggcgt tggcgaactg     240
agcgccgtca acggactggc aggaagctac gccgagaacc tgccagttgt cgaaattgtt     300
gggtcgccta cttctaaggt tcagaatgaa ggcaaatttg tgcaccatac tctggctgat     360
ggggatttta acattttat gaaaatgcat gaaccggtta ctgcggcccg cacgctgctg     420
acagcagaga atgctacggt tgagatcgac cgcgtcctgt ctgcgctgct gaaagagcgc     480
aagccggtat atatcaatct gcctgtcgat gttgccgcag cgaaagccga aaagccgtcg     540
ctgccactga aaaagaaaa cagcacctcc aatacatcgg accaggaaat tctgaataaa     600
atccaggaat cactgaagaa tgcgaagaaa ccgatcgtca tcaccggaca tgagatcatc     660
tcttttggcc tggaaaaaac ggtcacgcag ttcattctta agaccaaact gcctatcacc     720
accctgaact tcggcaaatc tagcgtcgat gaagcgctgc cgagttttct gggtatctat     780
aatggtaccc tgtccgaacc gaacctgaaa gaattcgtcg aaagcgcgga ctttatcctg     840
atgctgggcg tgaaactgac ggatagctcc acaggcgcat ttacccacca tctgaacgag     900
aataaaatga tttccctgaa tatcgacgaa ggcaaaatct ttaacgagcg catccagaac     960
ttcgattttg aatctctgat tagttcgctg ctggatctgt ccgaaattga gtataaaggt    1020
aaatatattg ataaaaaaca ggaggatttt gtgccgtcta tgcgctgct gagtcaggat    1080 cgtctgtggc aagccgtaga aaacctgaca cagtctaatg aaacgattgt tgcggaacag    1140
```

-continued

```
ggaacttcat ttttcggcgc ctcatccatt tttctgaaat ccaaaagcca tttcattggc    1200
caaccgctgt gggggagtat tggttatacc tttccggcgg cgctgggttc acagattgca    1260
gataaggaat cacgccatct gctgtttatt ggtgacggca gcctgcagct gactgtccag    1320
gaactggggc tggcgatccg tgaaaaaatc aatccgattt gctttatcat caataacgac    1380
ggctacaccg tcgaacgcga aattcatgga ccgaatcaaa gttacaatga catcccgatg    1440
tggaactata gcaaactgcc ggaatccttt ggcgcgacag aggatcgcgt ggtgagtaaa    1500
attgtgcgta cggaaaacga atttgtgtcg gttatgaaag aagcgcaggc tgacccgaat    1560
cgcatgtatt ggattgaact gatcctggca aaagaaggcg caccgaaagt tctgaaaaag    1620
atggggaaac tgtttgcgga gcaaaataaa agctaaggat cc                      1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
```

```
                  275                 280                 285
Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 37
<211> LENGTH: 1164
<212> TYPE: DNA
<213> ORGANISM: Escherichia coli

<400> SEQUENCE: 37
atgaacaact taatctgca cacccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg cacattctg     360 caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
```

-continued

```
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc acgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa atcatgaca ttacgttgga tgtcagccgc   1140
cgtatatacg aagccgcccg ctaa                                          1164
```

<210> SEQ ID NO 38
<211> LENGTH: 387
<212> TYPE: PRT
<213> ORGANISM: Escherichia coli

<400> SEQUENCE: 38

```
Met Asn Asn Phe Asn Leu His Thr Pro Thr Arg Ile Leu Phe Gly Lys
1               5                  10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
```

-continued

```
                260                 265                 270
Leu Thr Ala Met His Gly Leu Asp His Ala Gln Thr Leu Ala Ile Val
            275                 280                 285
Leu Pro Ala Leu Trp Asn Glu Lys Arg Asp Thr Lys Arg Ala Lys Leu
        290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
370                 375                 380
Ala Ala Arg
385
```

<210> SEQ ID NO 39
<211> LENGTH: 15
<212> TYPE: DNA
<213> ORGANISM: Artificial Sequence
<220> FEATURE:
<223> OTHER INFORMATION: Primer

<400> SEQUENCE: 39
acgggcggtg tgtac                                                    15

<210> SEQ ID NO 40
<211> LENGTH: 16
<212> TYPE: DNA
<213> ORGANISM: Artificial Sequence
<220> FEATURE:
<223> OTHER INFORMATION: Primer

<400> SEQUENCE: 40
gccagcagcc gcggta                                                   16

<210> SEQ ID NO 41
<211> LENGTH: 819
<212> TYPE: DNA
<213> ORGANISM: Enterococcus faecium

<400> SEQUENCE: 41
ccgcggcgtg ctgaaccgcg attactagcg attccggctt catgcaggcg agttgcagcc     60
tgcaatccga actgagagaa gctttaagag attagcttag cctcgcgact tcgcaactcg    120
ttgtacttcc cattgtagca cgtgtgtagc ccaggtcata gggggcatga tgatttgacg    180
tcatccccac cttcctccgg tttgtcaccg gcagtcttgc tagagtgccc aactgaatga    240
tggcaactaa caataagggt tgcgctcgtt gcgggactta acccaacatc tcacgacacg    300
agctgacgac aaccatgcac cacctgtcac tttgccccccg aaggggaagc tctatctcta    360
gagtggtcaa aggatgtcaa gacctggtaa ggttcttcgc gttgcttcga attaaaccac    420
atgctccacc gcttgtgcgg gccccgtca attcctttga gtttcaacct tgcggtcgta    480
ctccccaggc ggagtgctta atgcgttagc tgcagcactg aagggcggaa accctccaac    540
acttagcact catcgtttac ggcgtggact accagggtat ctaatcctgt ttgctcccca    600
cgctttcgag cctcagcgtc agttacagac cagagagccg ccttcgccac tggtgttcct    660
```

```
ccatatatct acgcatttca ccgctacaca tggaattcca ctctcctctt ctgcactcaa      720
gtctcccagt ttccaatgac cctccccggt tgagccgggg gctttcacat cagacttaag      780
aaaccgcctg cgctcgcttt acgccctaat aaatccgga                             819

<210> SEQ ID NO 42
<211> LENGTH: 1458
<212> TYPE: DNA
<213> ORGANISM: Enterococcus gallinarum

<400> SEQUENCE: 42
acgctggcgg cgtgcctaac atgcaagtcg aacgcttttt ctttcaccgg agcttgctcc       60
accgaaagaa aaagagtggc gaacgggtga gtaacacgtg ggtaacctgc ccatcagaag      120
gggataacac ttggaaacag gtgctaatac cgtataacac tattttccgc atggaagaaa     180
gttgaaaggc gcttttgcgt cactgatgga tggacccgcg gtgcattagc tagttggtga      240
ggtaacggct caccaaggcc acgatgcata gccgacctga gagggtgatc ggccacactg      300
ggactgagac acggcccaga ctcctacggg aggcagcagt agggaatctt cggcaatgga      360
cgaaagtctg accgagcaac gccgcgtgag tgaagaaggt tttcggatcg taaaactctg      420
ttgttagaga agaacaagga tgagagtaga acgttcatcc cttgacggta tctaaccaga      480
aagccacggc taactacgtg ccagcagccg cggtaatacg taggtggcaa gcgttgtccg      540
gatttattgg gcgtaaagcg agcgcaggcg gtttcttaag tctgatgtga aagcccccgg      600
ctcaaccggg gagggtcatt ggaaactggg agacttgagt gcagaagagg agagtggaat      660
tccatgtgta gcggtgaaat gcgtagatat atggaggaac accagtggcg aaggcggctc      720
tctggtctgt aactgacgct gaggctcgaa agcgtgggga gcgaacagga ttagataccc      780
tggtagtcca cgccgtaaac gatgagtgct aagtgttgga gggtttccgc ccttcagtgc      840
tgcagcaaac gcattaagca ctccgcctgg ggagtacgac cgcaaggttg aaactcaaag      900
gaattgacgg gggcccgcac aagcggtgga gcatgtggtt taattcgaag caacgcgaag      960
aaccttacca ggtcttgaca tcctttgacc actctagaga tagagcttcc ccttcggggg     1020
caaagtgaca ggtggtgcat ggttgtcgtc agctcgtgtc gtgagatgtt gggttaagtc     1080
ccgcaacgag cgcaacccct tattgttagt tgccatcattt agttgggcac tctagcgaga     1140
ctgccggtga caaaccggag gaaggtgggg atgacgtcaa atcatcatgc ccttatgac      1200 ctgggctaca cacgtgctac aatgggaagt acaacgagtt gcgaagtcgc gaggctaagc     1260
taatctctta aagcttctct cagttcggat tgtaggctgc aactcgccta catgaagccg     1320
gaatcgctag taatcgcgga tcagcacgcc gcggtgaata cgttcccggg ccttgtacac     1380
accgcccgtc acaccacgag agtttgtaac acccgaagtc ggtgaggtaa ccttttggag     1440
ccagccgcct aaggtgga                                                  1458

<210> SEQ ID NO 43
<211> LENGTH: 818
<212> TYPE: DNA
<213> ORGANISM: Enterococcus faecalis

<400> SEQUENCE: 43
ggcggagtgt cagtcggtgt gtaccggctg cgtgtacggg aggtgtgtac tgccgtcgta       60
aatgagagaa gctttaagag atttgcatga cctcgcggtc tagcgactcg ttgtacttcc      120
cattgtagca cgtgtgtagc ccaggtcata aggggcatga tgatttgacg tcatccccac      180
```

```
cttcctccgg tttgtcaccg gcagtctcgc tagagtgccc aactaaatga tggcaactaa        240
caataagggt tgcgctcgtt gcgggactta acccaacatc tcacgacacg agctgacgac        300
aaccatgcac cacctgtcac tttgtccccg aagggaaagc tctatctcta gagtggtcaa        360
aggatgtcaa gacctggtaa ggttcttcgc gttgcttcga attaaaccac atgctccacc        420
gcttgtgcgg gccccgtca attcctttga gtttcaacct tgcggtcgta ctccccaggc         480
ggagtgctta atgcgtttgc tgcagcactg aagggcggaa accctccaac acttagcact        540
catcgtttac ggcgtggact accagggtat ctaatcctgt ttgctcccca cgctttcgag        600
cctcagcgtc agttacagac cagagagccg ccttcgccac tggtgttcct ccatatatct        660
acgcatttca ccgctacaca tggaattcca ctctcctctt ctgcactcaa gtctcccagt       720
ttccaatgac cctccccggt tgagccgggg gctttcacat cagacttaag aaaccgcctg       780
cgctcgcttt acgcccaaaa atccgacaac gctgtacg                                818

<210> SEQ ID NO 44
<211> LENGTH: 794
<212> TYPE: DNA
<213> ORGANISM: Enterococcus faecium

<400> SEQUENCE: 44
ggcatgctga tccccgatta ctagcaattc cggcttcatg caggcgagtt ggaacctgca         60
atccgaactg agagaagctt taagagatta gcttagcctc gcgacttcgc gactcgttgt        120
acttcccatt gtagcacgtg tgtagcccag gtcataaggg gcatgatgat ttgacgtcat        180
ccccaccttc ctccggtttg tcaccggcag tcttgctaga gtgcccaact gaatgatggc        240
aactaacaat aagggttgcg ctcgttgcgg gacttaaccc aacatctcac gacacgagct        300
gacgacaacc atgcaccacc tgtcactttg ccccgaagg ggaagctcta tctctagagt         360
ggtcaaagga tgtcaagacc tggtaaggtt cttcgcgttg cttcgaatta aaccacatgc        420
tccaccgctt gtgcgggccc ccgtcaattc ctttgagttt caaccttgcg gtcgtactcc        480
ccaggcggag tgcttaatgc gttagctgca gcactgaagg gcggaaaccc tccaacactt        540
agcactcatc gtttacggcg tggactacca gggtatctaa tcctgtttgc tccccacgct        600
ttcgagcctc agcgtcagtt acagaccaga gagccgcctt cgccactggt gttcctccat        660
atatctacgc atttcaccgc tacacatgga attccactct cctcttctgc actcaagtct       720
cccagtttcc aatgaccctc cccggttgag ccggggcttt cacatcaga cttaagaaac        780 cgcctgcgct cgct                                                          794
```

US 7,659,104 B2

SOLVENT TOLERANT MICROORGANISMS AND METHODS OF ISOLATION

This application claims the benefit of U.S. Provisional Application No. 60/798,417, filed May 5, 2006.

FIELD OF THE INVENTION

The invention relates to the field of industrial microbiology. Specifically, microorganisms have been isolated that demonstrate high tolerance to alcohols, particularly butanols.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of butanols are known. For example, 1-butanol may be produced using the Oxo process, the Reppe process, or the hydrogenation of crotonaldehyde (*Ullmann's Encyclopedia of Industrial Chemistry*, 6$^{th}$ edition, 2003, Wiley-VCHVerlag GmbH and Co., Weinheim, Germany, Vol. 5, pp. 716-719). 2-Butanol may be produced using n-butene hydration (*Ullmann's Encyclopedia of Industrial Chemistry*, 6$^{th}$ edition, 2003, Wiley-VCHVerlag GmbH and Co., Weinheim, Germany, Vol. 5, pp. 716-719). Additionally, isobutanol may be produced using Oxo synthesis, catalytic hydrogenation of carbon monoxide (*Ullmann's Encyclopedia of Industrial Chemistry*, 6$^{th}$ edition, 2003, Wiley-VCHVerlag GmbH and Co., Weinheim, Germany, Vol. 5, pp. 716-719) or Guerbet condensation of methanol with n-propanol (Carlini et al., *J. Molec. Catal. A:Chem.* 220:215-220 (2004)). These processes use starting materials derived from petrochemicals, are generally expensive, and are not environmentally friendly.

Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway (Donaldson et al., copending and commonly owned U.S. patent application Ser. No. 11/527,995), a 2-butanol biosynthetic pathway (Donaldson et al., copending and commonly owned U.S. Patent Application No. 60/796,816), and an isobutanol biosynthetic pathway (Maggio-Hall et al., copending and commonly owned U.S. patent application Ser. No. 11/586,315) have been described. However, biological production of butanols is believed to be limited by butanol toxicity to the host microorganism used in the fermentation.

Strains of *Clostridium* that are tolerant to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., *Current Microbiology* 14(5):295-299 (1987)). Desmond et al. (*Appl. Environ. Microbiol.* 70(10):5929-5936 (2004)) report that overexpression of GroESL, a stress response protein, in *Lactococcus* lactis and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) have been described. However, for most microorganisms described in the art, growth is totally inhibited at a concentration of less than 2.0% w/v 1-butanol when grown in a liquid medium at 37° C. Moreover, microbial strains that have a tolerance to 2-butanol and isobutanol are not known in the art. Therefore, identification of microorganisms that have a high tolerance to 1-butanol, 2-butanol, and isobutanol would represent an advance in the art.

In addition, 2-butanone and ethanol are valuable compounds that can be produced by fermentation using microorganisms. 2-Butanone, also referred to as methyl ethyl ketone (MEK), is a widely used solvent and is the most important commercially produced ketone, after acetone. It is used as a solvent for paints, resins, and adhesives, as well as a selective extractant and activator of oxidative reactions. 2-butanone can be made by omitting the last step of the 2-butanol biosynthetic pathway (Donaldson et al., copending and commonly owned U.S. Patent Application No. 60/796,816). Ethanol is in high demand as an alternative fuel. Genetically modified strains of *E. coli* have been used as biocatalysts for ethanol production (Underwood et al., (2002) Appl. Environ. Microbiol. 68:6263-6272). A genetically modified strain of *Zymomonas mobilis* that has improved production of ethanol is described in US 2003/0162271 A1. Identification of microorganisms with improved tolerance to 2-butanone and ethanol would enhance the production of these compounds.

There is a need, therefore, for microbial host strains that are more tolerant to butanols and may be used for the bioproduction of butanols to high titer. The present invention addresses this need through the discovery of butanol tolerant microorganisms and development of methods for their isolation. In addition the discovered microorganisms have increased tolerance to 2-butanone and ethanol.

SUMMARY OF THE INVENTION

The invention relates to butanol tolerant microorganisms, particularly members of the genus *Enterococcus*, and methods for the isolation of the same. Microbial consortia were enriched and selected for tolerance to butanol. Several species of *Enterococcus* were isolated that demonstrated tolerance to concentrations of butanol of at least 2.5% w/v 1-butanol when grown on a solid medium at 37° C.

Accordingly, in one embodiment the invention provides a method for the isolation of a butanol tolerant microorganism comprising:

a) providing a microbial sample comprising a microbial consortium;

b) contacting the microbial consortium in a growth medium comprising a fermentable carbon source until the members of the microbial consortium are growing;

c) contacting the growing microbial consortium of step (b) with butanol; and d) isolating the viable members of step (c) wherein a butanol tolerant microorganism is isolated. In a preferred embodiment viable members of the microbial consortium are isolated by a process comprising the steps of:

i) growing the viable members of the consortium that has been challenged with butanol in a liquid medium in the absence of butanol; whereby the viable members multiply;
ii) growing the cells of step (i) in the presence of butanol; and
iii) collecting the cells of step (ii) that grow in the presence of butanol wherein a butanol tolerant microorganism is isolated.

In another embodiment the invention provides butanol tolerant microorganisms isolated by the processes of the invention where preferred butanol tolerant microorganisms belong to the genus *Enterococcus*.

In another embodiment the invention provides a method for the isolation of a butanol tolerant *Enterococcus* comprising:
  a) providing a microbial sample comprising a microbial consortium;
  b) enriching the microbial consortium for the presence of *Enterococcus* in a growth medium comprising:
    i) a fermentable carbon source; and
    ii) a competitor growth inhibitor;
    to generate an *Enterococcus* enriched culture in which members of the *Enterococcus* enriched culture are growing;
  c) contacting the growing *Enterococcus* enriched culture of step (b) with butanol; and
  d) isolating the viable members of step (c) wherein a butanol tolerant *Enterococcus* is isolated.

In another embodiment the invention provides a butanol tolerant *Enterococcus* having the following characteristics:
  i) is a facultative anaerobe; and
  ii) is Gram-positive; and
  iii) is non-motile; and
  iv) has spherical or ovoid cell morphology; and
  v) has ability to initiate growth in 6.5% sodium chloride broth and in broth at pH 9.6; and
  vi) is tolerant to at least 2.5% w/v butanol when grown on a solid medium.

In another embodiment the invention provides a butanol tolerant *Enterococcus* selected from the group consisting of ATCC PTA-7478 (*Enterococcus faecium* PN0110), ATCC_PTA-7479 (*Enterococcus gallinarium* PN0048), ATCC PTA-7477 (*Enterococcus faecalis* PN0197-10) and ATCC PTA-7480 (*Enterococcus faecium* PN0133).

In another embodiment the invention provides a method for the production of 2-butanone comprising:
  a) providing an *Enterococcus* comprising genetic constructs encoding a 2-butanone biosynthetic pathway, having the following characteristics:
    i) is a facultative anaerobe; and
    ii) is Gram-positive; and
    iii) is non-motile; and
    iv) has spherical or ovoid cell morphology; and
    v) has ability to initiate growth in 6.5% sodium chloride broth and in broth at pH 9.6; and
    vi) is tolerant to at least 2.5% w/v butanol when grown on a solid medium and
  b) growing the *Enterococcus* of step (a) under conditions whereby 2-butanone is produced.

BRIEF DESCRIPTION BIOLOGICAL DEPOSITS AND SEQUENCE DESCRIPTIONS

The various embodiments of the invention can be more fully understood from the following detailed description, biological deposits, and the accompanying sequence descriptions, which form a part of this application.

Applicants made the following biological deposits under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Enterococcus faecium* PN0110 | ATCC: PTA-7478 | Apr. 7, 2006 |
| *Enterococcus gallinarium* PN0048 | ATCC: PTA-7479 | Apr. 7, 2006 |
| *Enterococcus faecalis* PN0197-10 | ATCC: PTA-7477 | Apr. 7, 2006 |
| *Enterococcus faecium* PN0133 | ATCC: PTA-7480 | Apr. 7, 2006 |

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Gene and Protein SEQ ID Numbers
for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Gene and Protein SEQ ID Numbers
for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *E. coli* ilvC (acetohydroxy acid reductoisomerase) | 31 | 32 |
| *E. coli* ilvD (acetohydroxy acid dehydratase) | 33 | 34 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

SEQ ID NOs:39 and 40 are the nucleotide sequences of primers used to amplify the 16S rRNA genes of butanol tolerant strains, as described in Example 1.

SEQ ID NOs:41-44 are the nucleotide sequences of the 16S rRNA genes of butanol tolerant *Enterococcus* strains, isolated as described in Examples 1-4.

DETAILED DESCRIPTION OF THE INVENTION

The present invention provides microorganisms that demonstrate high tolerance to alcohols, particularly butanols, as well as to 2-butanone and ethanol. The microorganisms of the invention are able to grow in the presence of 2.5% w/v or greater 1-butanol, 2-butanol, isobutanol, 2-butanone, or ethanol on a solid medium. Additionally, the invention provides a method for the isolation of butanol tolerant microorganisms. These butanol tolerant microorganisms may be genetically engineered to comprise a butanol biosynthetic pathway or a 2-butanone biosynthetic pathway, and used for the bioproduction of 1-butanol, 2-butanol, isobutanol, or 2-butanone to high titer.

The following definitions and abbreviations are to be used for the interpretation of the claims and the specification.

The term "butanol" as used herein, refers to 1-butanol, 2-butanol, isobutanol, or mixtures thereof.

The terms "butanol tolerant microorganism" and "tolerant" when used to describe a microorganism of the invention, refers to a bacterium or yeast that exhibits growth in the presence of 2.5% w/v or greater 1-butanol, 2-butanol, or isobutanol when grown on a solid medium at 37° C., or in the presence 2.0% w/v or greater 1-butanol, 2-butanol, or isobutanol when grown in a liquid medium at 37° C.

The term "microbial consortium" refers to a heterogeneous group of microbes with different genotypes. By way of example, a microbial consortium may be an environmental sample such as a wastewater sludge or soil or compost or contaminated water samples; a chemically mutagenized microbial population of a pure bacterial strain; a microbial strain containing a multicopy plasmid library; of a population of transposon tagged mutants of a particular strain.

The term "environmental sample" refers to a sample obtained from the environment. In particular, the environmental sample may be wastewater sludge or other sample obtained from an environment where there has been exposure to butanol and/or other solvents. The environmental sample comprises a microbial consortium.

The term "enriching" as applied to a microbial culture and particularly the culturing of a microbial consortium refers to the practice of supplying the cells of the consortium or microbial culture with an excess of growth nutrients to enhance or encourage the growth of the cells.

The terms "fermentable carbon source", "carbon substrate" or "fermentable carbon substrate" are used interchangeably and refer to a source of carbon that is readily utilized by a microbial consortium. Fermentable carbon sources include, but are not limited to, monosaccharides, oligosaccharides, polysaccharides, and one-carbon substrates or mixtures thereof. A non-limiting list of preferred fermentable carbon sources includes simple sugars, such as glucose, fructose, and sucrose; and carboxylic acids such as fatty acids, butyric acid, and valeric acid.

The term "aerobic conditions" means growth conditions in the presence of oxygen.

The term "anaerobic conditions" means growth conditions in the absence of oxygen.

The term "microaerophilic conditions" means growth conditions with low levels of oxygen (i.e., below normal atmospheric oxygen levels).

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "2-butanone biosynthetic pathway" refers to the enzyme pathways to produce 2-butanone from pyruvate.

The term "isobutanol biosynthetic pathway" refers to an enzyme pathway to produce isobutanol from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature 1992*, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and H$_2$O. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417-484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate. Suitable acetolactate synthase enzymes are available from a number of sources, for example, *Bacillus subtilis* (GenBank Nos: AAA22222 NCBI (National Center for Biotechnology Information) amino acid sequence, L04470 NCBI nucleotide sequence), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtiiis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus* lactis (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook, J., Fritsch, E. F. and Man iatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The term "invention" or "present invention" as used herein is meant to apply generally to all embodiments of the invention as described in the claims as presented or as later amended and supplemented, or in the specification.

In one embodiment the present invention provides a method for the isolation of butanol tolerant microorganisms. The method comprises enriching a microbial consortium under growth conditions and contacting the enriched consortium with butanol, as described in detail below. Microorganisms that demonstrate high tolerance to alcohols, particularly butanols, identified by the method of the invention, are also provided. These butanol tolerant microorganisms may be genetically engineered to comprise a butanol biosynthetic pathway and used for the bioproduction of 1-butanol, 2-butanol, or isobutanol to high titer.

Isolation of Butanol Tolerant Microorganisms

Butanol tolerant microorganisms may be isolated from environmental samples such as wastewater sludge and samples from other environments where there is exposure to butanol and/or other solvents. For example, environmental samples may be obtained from wastewater treatment facilities at chemical plants. Industrial wastewater bioreactors are particularly good sources of environmental samples of microorganisms with desirable resistance phenotypes because of the long-term growth in the presence of various organic solvents (Bramucci et al., *Trends Biotechnol.* 18:501-505 (2000)). Butanol tolerant microorganisms may be isolated from other microbial samples as well. For example, the microbial sample may be a chemically mutagenized microbial population of a pure bacterial strain, a microbial strain containing a multi-copy plasmid library, or a transposon tagged mutants of a particular strain. Any of these microbial samples including a mixed population is said to include a microbial consortium.

In one embodiment of the present invention, the microbial sample is cultured in a growth medium to enrich the microbial consortium contained therein until the members of the consortium are growing. In one embodiment the cultures are growing in log phase. The growth medium comprises a fermentable carbon source and may include suitable levels of nitrogen, phosphorus, sulfur, and salts. Suitable levels of these nutrients necessary for growth of the microbial consortium are well known to those skilled in the art, and non-limiting examples are provided below. The fermentable carbon source may be any carbon source that is readily metabolized by the members of the microbial consortium, including but not limited to, sucrose, fructose, glucose, and mixtures thereof. The fermentable carbon source may also be a carboxylic acid such as a fatty acid, butyric acid or valeric acid. Typically, the carbon source is present at a concentration from about 0.1% weight/volume w/v to about 1.5% w/v. The nitrogen source may be any suitable nitrogen source, including but not limited to, ammonium salts or yeast extract. The nitrogen source is typically present in the growth medium at a concentration of about 10 mM. Phosphorus may be present in the medium in the form of phosphate salts, such as sodium and potassium phosphates, which are typically present in the growth medium at a concentration of about 50 mM. Sulfur may be present in the medium in the form of sulfate salts, such as sodium or ammonium sulfates, which are typically present in the growth medium at a concentration of about 10 mM. Additional salts include, but are not limited to, magnesium chloride, calcium chloride, manganese chloride, ferric chloride, ferrous chloride, zinc chloride, cupric chloride, cobalt chloride, and sodium molybdate. These salts are typically present in the growth medium at a concentration of about 1 mM to about 2 mM. The growth medium may also contain vitamins such as thiamine hydrochloride.

The enrichment culture is grown at a temperature of about 25° C. to about 60° C. for a time sufficient for the members of the microbial consortium in the sample to exhibit growth, typically about 12 hours to about 24 hours. The culture may be grown under anaerobic, microaerophilic, or aerobic conditions, with or without agitation. As is readily understood by the skilled person, anaerobic conditions are those that are devoid of oxygen, aerobic conditions are those that contain oxygen and microaerophilic conditions are those where oxygen is present at a level below that found in air, ie. less than 21%. Growth of the culture may be monitored by measuring the optical density, typically at a wavelength of 600 nm.

The growing enrichment culture is then contacted with butanol. This contacting may be done by diluting the enrichment culture with a fresh growth medium that contains butanol. It is particularly suitable if the enrichment culture is growing in log phase at this point. The butanol concentration used is about 0.8% w/v to about 3.0% w/v, preferably about 0.8% w/v to about 2.0% w/v. In one embodiment, the butanol is predominantly 1-butanol. In another embodiment, the butanol is predominantly 2-butanol. In another embodiment, the butanol is predominantly isobutanol. As used herein, predominantly means at least about 90% by weight of the total butanol. Additionally, mixtures comprising various combinations of two or more of 1-butanol, 2-butanol, and isobutanol may be used. The culture is grown for a period of time until significant growth is observed. Optionally, the cultures that demonstrate significant growth may be contacted with butanol again one or more times to select for increased tolerance to butanol. Each contacting may be made with progressively higher butanol concentrations.

The microbial consortium that was contacted with butanol is then separated to isolate individual strains. Multiple means of cell isolation are know to those skilled in the art involving either liquid or solid media. For example, the microbial consortium that was contacted with butanol may be plated onto a solid medium, for example nutrient agar, Luria Bertani (LB) agar, modified LB agar (i.e., LB agar supplemented with a fermentable carbon source and salts), or minimal enrichment medium with agar, which may or may not contain butanol. If butanol is present in the solid medium, its concentration is typically about 1.2% w/v to about 3% w/v. The culture is grown until colonies are formed. The colonies are then isolated using methods known in the art to provide a butanol tolerant microorganism. For example, the colonies from the solid medium may be collected and identified using methods known in the art, as described below. Alternatively, the colonies from the solid medium may be inoculated into a growth medium (e.g., minimal enrichment medium), either liquid or solid, that does not contain butanol. After growth, the cells may be collected and identified. Optionally, the cells from the colonies may be grown in the presence of butanol, either in liquid or solid growth medium (e.g., minimal enrichment medium). Typically, the butanol concentration in the medium is about 1.2% w/v to about 3% w/v. The cells that grow in the presence of butanol are collected. The isolated microorganisms may be identified using methods known in the art, such as 16S ribosomal RNA (rRNA) gene sequencing, fatty acid profile analysis, or ribotyping.

The butanol tolerant microorganisms isolated by the method of the present invention are tolerant to at least 2.5% butanol (i.e., 1-butanol, 2-butanol, or isobutanol) when grown on a solid medium at 37° C., or to at least 2.0% w/v butanol when grown in a liquid medium at 37° C. It should be noted that the butanol tolerance of microorganisms is typically higher when grown on a solid medium than when grown on a liquid medium. Additionally, the butanol tolerance of microorganisms is dependent on the growth temperature, typically being higher at lower growth temperatures. Microorganisms isolated by contacting the enriched microbial consortium with one butanol are generally also tolerant to other butanols. For example, microorganisms isolated using 1-butanol are also tolerant to 2-butanol and isobutanol.

The enrichment culture may also be grown and contacted with butanol in a continuous culture in a chemostat bioreactor. The cells in a chemostat bioreactor can be grown at various growth rates by appropriate adjustment of the dilution rate. Chemostat cultures can be precisely controlled for aeration and pH, leading to higher cell densities. Additionally, butanol can be gradually added in increasing concentration by adjusting feed composition. After contacting the enrichment culture with butanol in the bioreactor, the butanol tolerant microorganisms are isolated and identified as described above.

Unexpectedly, the majority of the butanol tolerant microorganisms identified using the method of the present invention in the examples herein were bacteria belonging to the genus *Enterococcus*. *Enterococcus* are facultively anaerobic, Gram-positive, non-motile, spherical or ovoid cells having the ability to initiate growth in 6.5% sodium chloride broth and in broth at pH 9.6 (*Bergey's Manual of Systematic Bacteriology*, Vol 2, Sneath et al., Eds.; Williams & Wilkins, Baltimore, Md., 1986, pp. 1063-1065). The butanol tolerant *Enterococcus* strains of the present invention are further characterized by the 16S rRNA gene sequences given as SEQ ID NOs:41, 42, 43, and 44.

The present method for isolation of butanol tolerant microorganisms may be modified to selectively isolate butanol tolerant *Enterococcus*. In this embodiment, the microbial consortium from the environmental sample is enriched for the presence of *Enterococcus* in a growth medium comprising a fermentable carbon source, suitable levels of nitrogen, phosphorus, sulfur, and salts, as described above, and a "competitor growth inhibitor" which functions to inhibit the growth of microorganisms other than *Enterococcus*. Suitable competitor growth inhibitors include, but are not limited to, bile, azide, and mixtures thereof. The optimum amount of the competitor growth inhibitor to use will depend on the microbial consortium and the type of inhibitor, and can be determined using routine experimentation. The *Enterococcus* enriched culture is grown to log phase and contacted with butanol as described above. The butanol tolerant *Enterococcus* strains are then isolated and identified as described above.

The isolated butanol tolerant *Enterococcus* strains may be genetically engineered to comprise genetic constructs encoding a butanol biosynthetic pathway and grown under suitable conditions to produce butanol. The butanol biosynthetic pathway may be a 1-butanol, 2-butanol, or isobutanol biosynthetic pathway.

1-Butanol Biosynthetic Pathway

A biosynthetic pathway for the production of 1-butanol is described by Donaldson et al. in copending and commonly owned U.S. patent application Ser. No. 11/527,995, which is incorporated herein by reference. This biosynthetic pathway comprises the following substrate to product conversions:
 a) acetyl-CoA to acetoacetyl-CoA, as catalyzed for example by acetyl-CoA acetyltransferase encoded by the genes given as SEQ ID NO:1 or 3;
 b) acetoacetyl-CoA to 3-hydroxybutyryl-CoA, as catalyzed for example by 3-hydroxybutyryl-CoA dehydrogenase encoded by the gene given as SEQ ID NO:5;
 c) 3-hydroxybutyryl-CoA to crotonyl-CoA, as catalyzed for example by crotonase encoded by the gene given as SEQ ID NO:7;
 d) crotonyl-CoA to butyryl-CoA, as catalyzed for example by butyryl-CoA dehydrogenase encoded by the gene given as SEQ ID NO:9;
 e) butyryl-CoA to butyraldehyde, as catalyzed for example by butyraldehyde dehydrogenase encoded by the gene given as SEQ ID NO:11; and
 f) butyraldehyde to 1-butanol, as catalyzed for example by 1-butanol dehydrogenase encoded by the genes given as SEQ ID NO:13 or 15.

The pathway requires no ATP and generates $NAD^+$ and/or $NADP^+$, thus, it balances with the central metabolic routes that generate acetyl-CoA.

2-Butanol and 2-Butanone Biosynthetic Pathway Biosynthetic pathways for the production of 2-butanol and 2-butanone are described by Donaldson et al. in copending and commonly owned U.S. Patent Application No. 60/796,816, which is incorporated herein by reference. One 2-butanol biosynthetic pathway comprises the following substrate to product conversions:
 a) pyruvate to alpha-acetolactate, as catalyzed for example by acetolactate synthase encoded by the gene given as SEQ ID NO:19;
 b) alpha-acetolactate to acetoin, as catalyzed for example by acetolactate decarboxylase encoded by the gene given as SEQ ID NO:17;
 c) acetoin to 2,3-butanediol, as catalyzed for example by butanediol dehydrogenase encoded by the gene given as SEQ ID NO:21;
 d) 2,3-butanediol to 2-butanone, catalyzed for example by butanediol dehydratase encoded by genes given as SEQ ID NOs:23, 25, and 27; and
 e) 2-butanone to 2-butanol, as catalyzed for example by 2-butanol dehydrogenase encoded by the gene given as SEQ ID NO:29.
 Omitting the last step (e) of the above pathway provides a biosynthetic pathway for production of 2-butanone, also known as methyl ethyl ketone (MEK), Isobutanol Biosynthetic Pathway Biosynthetic pathways for the production of isobutanol are described by Maggio-Hall et al. in copending and commonly owned U.S. patent application Ser. No. 11/586,315, which is incorporated herein by reference. One isobutanol biosynthetic pathway comprises the following substrate to product conversions:

a) pyruvate to acetolactate, as catalyzed for example by acetolactate synthase encoded by the gene given as SEQ ID NO:19;

b) acetolactate to 2,3-dihydroxyisovalerate, as catalyzed for example by acetohydroxy acid isomeroreductase encoded by the gene given as SEQ ID NO:31;

c) 2,3-dihydroxyisovalerate to α-ketoisovalerate, as catalyzed for example by acetohydroxy acid dehydratase encoded by the gene given as SEQ ID NO:33;

d) α-ketoisovalerate to isobutyraldehyde, as catalyzed for example by a branched-chain keto acid decarboxylase encoded by the gene given as SEQ ID NO:35; and e) isobutyraldehyde to isobutanol, as catalyzed for example by a branched-chain alcohol dehydrogenase encoded by the gene given as SEQ ID NO:37.

Construction of *Enterococcus* Hosts for Butanol Production

Recombinant, butanol tolerant *Enterococcus* strains containing the necessary genes that will encode one of the enzymatic pathways for the conversion of a fermentable carbon substrate to butanol may be constructed using techniques well known in the art. The genome sequences of *Enterococcus faecalis* and *Enterococcus faecium* are known (National Center for Biotechnology Information (NCBI) database). These bacteria have a G+C content of 37%. *Enterococcus gallinarum* is closely related to *Enterococcus faecalis* and *Enterococcus faecium*.

In the present invention, genes encoding the enzymes of one of the butanol biosynthetic pathways described above may be isolated from various sources (see above). Methods of obtaining desired genes from a bacterial genome are common and well known in the art of molecular biology. For example, if the sequence of the gene is known, primers may be designed and the desired sequence amplified using standard primer-directed amplification methods such as polymerase chain reaction (U.S. Pat. No. 4,683,202) to obtain amounts of DNA suitable for cloning into transformation vectors. If a gene that is heterologous to a known sequence is to be isolated, suitable genomic libraries may be created by restriction endonuclease digestion and may be screened with probes having complementary sequence to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available.

Once the relevant pathway genes are identified and isolated they may be inserted in a vector and transformed into a butanol tolerant *Enterococcus* host by means well known in the art. Vectors useful for the transformation of *Enterococcus* are known (see below). Typically the vector contains sequences directing transcription and translation of the inserted DNA fragment, a selectable marker, and sequences allowing autonomous replication or chromosomal integration. Suitable vectors comprise a region 5' of the inserted DNA fragment which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific production host.

Initiation control regions or promoters, which are useful to drive expression of the relevant pathway coding regions in the desired *Enterococcus* host cell, may be obtained from other lactic acid bacteria or other Gram-positive organisms. A non-limiting example is the nisA promoter from *Lactococcus*. Termination control regions may also be derived from various genes native to the preferred hosts or related bacteria. Optionally, a termination site may be unnecessary, however, it is most preferred if included.

The *Enterococcus* genus belongs to the *Lactobacillales* family and many plasmids and vectors used in the transformation of *Lactobacillus*, *Bacillus subtilis*, and *Streptococcus* may be used for *Enterococcus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. Appl. Environ. Microbiol. 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Expression vectors for *E. faecalis* using the nisA promoter from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.* 72:334-345 (2006)).

The various genes for a butanol biosynthetic pathway may be assembled into any suitable vector, such as those described above. The codons can be optimized for expression based on the codon index deduced from the genome sequences of *Enterococcus faecalis* or *Enterococcus faecium*. The plasmids may be introduced into the butanol tolerant host cell using methods known in the art, such as electroporation, as described by Cruz-Rodz et al. (*Molecular Genetics and Genomics* 224:1252-154 (1990)) or conjugation, as described by Tanimoto et al. (*J. Bacteriol.* 184:5800-5804 (2002)) and Grohamann et al. (*Microbiol. Mol. Biol. Rev.* 67:277-301 (2003)).

Fermentation Media

Fermentation media for the production of butanol must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Industrial Batch and Continuous Fermentations

Butanol may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Butanol may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol may be practiced using either batch, fed-batch or continuous processes and that any known mode of fermentation would be suitable. Additionally, it is contemplated that cells may be immobilized on a substrate as whole cell catalysts and subjected to fermentation conditions for butanol production.

Methods for Butanol Isolation from the Fermentation Medium

The bioproduced butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec' means second(s), "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "rpm" means revolutions per minute, "w/v" means weight/volume, "OD" means optical density, "$OD_{600}$" means optical density measured at a wavelength of 600 nm, "$OD_{595}$" means optical density measured at a wavelength of 595 nm, "$IC_{50}$" means the concentration of butanol that causes a 50% inhibition of growth, "GCMS" means gas chromatography-mass spectrometry, and "HPLC" means high performance liquid chromatography.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Isolation of Butanol Tolerant Microorganisms

The purpose of this Example was to isolate butanol tolerant microorganisms. Environmental samples were obtained from several wastewater treatment sites and were grown in enrichment cultures containing 1-butanol in shake flasks. A butanol tolerant bacterial strain was isolated and identified as *Enterococcus faecium*.

Environmental sludge samples were obtained from wastewater treatment facilities at several E.I. du Pont de Nemours and Company sites. Enrichment cultures were established for each sample by inoculating a 125-mL screw cap Erlenmeyer flask with 1 mL of a sludge sample in 10 mL of minimal enrichment medium (i.e., 10 mM ammonium sulfate, 50 mM potassium phosphate buffer, pH 7.0, 2 mM $MgCl_2$, 0.7 mM $CaCl_2$, 50 µM $MnCl_2$, 1 µM $FeCl_3$, 1 µM $ZnCl_2$, 1.72 µM $CuCl_2$, 2.53 µM $CoCl_2$, 2.42 µM $Na_2MoO_4$, 2 µM thiamine hydrochloride, 0.5% glucose, 0.5% fructose, 0.5% sucrose and 0.1% yeast extract). The enrichment cultures were incubated at 37° C. with shaking. After 24 h of incubation, the enrichment cultures were diluted 1:10 into fresh medium that contained 0.8%, 1.2% or 1.6% w/v 1-butanol (Sigma Chemical Co.; molecular biology grade (greater than or equal to 99% purity)). Incubation continued under the same conditions. Cultures with the highest level of 1-butanol allowing significant growth (e.g., a culture with an initial $OD_{600}$ of approximately 0.1 that increased within 24 to 48 h to an $OD_{600}$ of approximately 1.0) were then diluted 1:10 into fresh medium that contained higher levels of 1-butanol to select for increased tolerance to 1-butanol. Most of the enrichment cultures grew in the presence of 1.2% 1-butanol and enrichment cultures from some sites grew in the presence of 1.6% 1-butanol. However, none of the enrichment cultures grew in the presence of 2.0% 1-butanol in a liquid medium.

Pure strains of 1-butanol resistant bacteria were isolated from the enrichment cultures as follows. The cells grown in an enrichment culture containing 1.2% or 1.6% 1-butanol were serially diluted, and the serial dilutions were plated on Luria Bertani (LB) agar medium, modified LB agar (i.e., LB agar supplemented with 0.5% sucrose, 0.5% glucose, 0.5% fructose, 0.5% sodium pyruvate, 2 mM $MgCl_2$, 0.7 mM $CaCl_2$, 50 µM $MnCl_2$, 1 µM $FeCl_3$, 1 µM $ZnCl_2$, 1.72 µM $CuCl_2$, 2.53 µM $CoCl_2$, 2.42 µM $Na_2MoO_4$ and 2 µM thiamine hydrochloride) or minimal enrichment medium with 2.0% Difco™ Agar Noble, (BD Diagnostic Systems, Sparks, Md.), all without 1-butanol. Colonies were then inoculated from the agar medium into minimal enrichment medium (described above) without 1-butanol in the wells of a microtiter plate. The cells in each well were subcultured in separate microtiter plates with and without 1-butanol to identify 1-butanol-tolerant isolates. The amount of 1-butanol used to challenge the isolates ranged from 1.2% to 3.0% w/v. Several isolates from the enrichments displayed growth in 2.0% or higher 1-butanol in a liquid medium at 37° C. The $IC_{50}$ values of the isolated strains able to grow in liquid medium containing at least 2.0% 1-butanol were determined as follows. The growth was monitored (by $OD_{600}$) of isolates cultured in S30L medium (i.e., 10 mM ammonium sulfate, 5 mM potassium phosphate buffer, pH 7.0, 50 mM MOPS, pH 7.0, 2 mM $MgCl_2$, 0.7 mM $CaCl_2$, 50 µM $MnCl_2$, 1 µM $FeCl_3$, 1 µM $ZnCl_2$, 1.72 µM $CuCl_2$, 2.53 µM $CoCl_2$, 2.42 µM $Na_2MoO_4$, 2 µM thiamine hydrochloride, 0.01 M glucose, and 0.2% yeast extract) at 37° C. in the absence (control) and in the presence of from 1.2% to 3.0% w/v of 1-butanol and the doubling time for each culture was calculated from the logarithmic part of the growth curve (doubling time=0.693/growth rate). The percent growth inhibition caused by 1-butanol in the sample flasks was determined by subtracting the percent growth ([doubling time of the control flask/doubling time of the sample flask]×100) from 100%. The $IC_{50}$ was the concentration of butanol that caused 50% growth inhibition and was determined by plotting the concentration of butanol versus percent inhibition. The results for a representative strain that was able to grow on solid medium containing 2.5% w/v 1-butanol at 37° C. are summarized in Table 4. Higher $IC_{50}$ values were obtained when the strains were cultured at 30° C. (data not shown). The isolates were identified by sequencing the product that resulted from polymerase chain reaction (PCR) amplification of the 16S rRNA genes in DNA that was extracted from each isolate. DNA was extracted from each of the 1-butanol tolerant strains. Each isolate was processed using a commercial kit (Ultraclean Microbial Genomic DNA Isolation Kit, obtained from Mo Bio Laboratories, Inc, Carlsbad, Calif., Part No. 12224-50). The 16S rRNA genes of the isolates were amplified by PCR using HotStar Taq (Qiagen, Valencia, Calif.; Catalog No. 203446) with primers JCR14 (ACGGGCGGTGTGTAC), given as SEQ ID NO:39 and JCR15 (GCCAGCAGCCGCGGTA), given as SEQ ID NO:40. The PCR conditions were 15 min at 95° C., followed by 30 cycles at 94° C. for 45 sec, 55° C. for 1 min, and 72° C. for 1 min, followed by 10 min at 72° C. The PCR products were purified and sequenced. Each sequence was used as the query sequence for a BLAST search of GenBank for the most similar previously identified 16S rRNA gene sequence. The sequence of the rRNA gene of the isolated strain that was designated PN0110 (SEQ ID NO: 41) matched the known rRNA sequence for *Enterococcus faecium* (see Table 4).

TABLE 4

Butanol Tolerant Bacterial Strain Isolated from Environmental Samples

| illsolate | Phylotype | ATTC No. | 16S rRNA Sequence | $IC_{50}$ (%) 1-butanol at 37° C. |
|---|---|---|---|---|
| PN0110 | *Enterococcus faecium* | PTA-7478 | SEQ ID NO: 41 | 1.7 |

Example 2

Isolation of Butanol Tolerant Bacterial Strains Using Continuous Culture

The purpose of this Example was to isolate butanol tolerant bacterial strains. Environmental samples were obtained from several wastewater treatment sites and were grown in the presence of 1-butanol in continuous culture in a chemostat bioreactor. Several 1-butanol tolerant bacterial strains were isolated and identified as different species of *Enterococcus*.

An Appilikon Fermentor (Appilikon Inc., Clinton, N.J.) was operated as an anaerobic chemostat. This bioreactor system was composed of a 1-L dished bottom reactor, Controller ADI 1032 P100, and stirrer unit with marine and turbine impellers. Bio Controller ADI 1030 Z510300020 with appropriate sensors was used to monitor pH, dissolved oxygen, and temperature. A Cole Parmer pump and pump head (Cole Parmer Instrument Co., Vernon Hills, Ill.) were used for addition of acid and base to maintain the culture medium at pH 7.0. The temperature was maintained at 37° C. using a circulating water bath. The culture medium (S20 medium) consisted of 5 mM potassium phosphate buffer, pH 7.0, 10 mM ammonium sulfate, 0.1% yeast extract, 0.1% caseamino acids, 100 mM MOPS, 2 mM $MgCl_2$, 0.7 mM $CaCl_2$, 0.05 mM $MnCl_2$, 0.001 mM $ZnCl_2$, 0.002 mM thiamine hydrochloride, 1.72 µM $CuCl_2$, 2.53 µM $CoCl_2$, 2.42 µM $Na_2MoO_4$, 25 mM glucose, 12.5 mM sucrose, and 12.5 mM fructose, and a volume of 500 mL of this medium was used in the bioreactor. The bioreactor was operated with a feed rate in the range of 0.1 to 1.0 mL/minute and a stirrer speed of 50 rpm.

The bioreactor was inoculated with a mixture of several wastewater sludge samples obtained from different wastewater treatment facilities at several E.I. du Pont de Nemours and Company sites. After a short period of batch mode operation, the bioreactor was operated in continuous feed mode. 1-Butanol was added to the bioreactor as part of the influent culture medium. The level of 1-butanol in the bioreactor was 0% when the bioreactor was switched from batch mode to continuous feed mode and then 1-butanol was gradually increased to 2.5% in the bioreactor. The flow rate of the medium was in the range of 0.1 to 1.0 mL/min.

Cell density in the bioreactor was monitored by measuring the optical density at 600 nm. The 1-butanol in the feed and effluent was determined by GCMS using an HP6890 Gas Chromatograph with 5973 Mass Detector (Agilent Technologies, Inc, Wilmington, Del.). The GC column was a DB-WAX, 30 m×0.32 mm ID×0.25 µm column (J&W Scientific, Inc., Folsom, Calif.). Alternatively, samples were filtered (Acrodisc CR PTFE 0.2 µm filters) and analyzed by HPLC using a Shodex® SH1011 column (8 mm ID×300 mm length; Shoko America Inc., Colorado Springs, Colo.) with a Shodex® SH-G guard column. The mobile phase was 0.01 N sulfuric acid. The column temperature was 50° C. and a flow rate of 0.5 mL/min was used. For detection, a photometric detector at 210 nm and a refractive index detector were used. The sample injection volume was 10 µL.

After an initial adjustment period, the amount of 1-butanol entering the bioreactor through the feed was gradually increased to reach a final 1-butanol concentration in the culture medium of 2.5% w/v. During this same period, the amount of glucose in the bioreactor effluent was monitored. Increasing the amount of 1-butanol in the feed resulted in a decrease in cell density and a concomitant decrease in glucose utilization. Continued incubation resulted in the cell density and glucose utilization again increasing after adaptation to a higher level of 1-butanol. For example, increasing 1-butanol to 1.6% resulted in the cell density decreasing to less than 1.5 $OD_{600}$ with a corresponding decrease in glucose utilization. However, continued incubation resulted in the cell density increasing to 2.3 $OD_{600}$ with a corresponding increase in glucose consumption.

Phylogenetic characterization of the microbial consortium in the anaerobic bioreactor and isolation of pure strains of 1-butanol resistant bacteria from this bioreactor were performed as follows. Samples of cells taken from the bioreactor at various times and from the bioreactor waste jug were serially diluted, and the serial dilutions were plated on S20 agar medium (S20 medium with 1.6% DifCo™ Agar, Noble-Solidifying agent) without 1-butanol. Colonies were then inoculated from the S20 agar medium into 1.2 mL of S20 medium without 1-butanol in the wells of a square-well microtiter plate (Beckman Coulter Inc, Fullerton, Calif.; Catalog No. 069681). The square-well microtiter plate was sealed with an adhesive cover (Beckman Coulter Inc.; Catalog No. 538619) and incubated at 37° C. with shaking for up to 72 h. The square-well microtiter plate was used to make a master plate by dispensing 200 µL of culture from each square well into a corresponding well in a "U-bottom" microtiter plate (VWR Scientific Products, West Chester, Pa.; Catalog No. 62409-052). The cells in each well were then subcultured into 200 µL of S20 medium in the wells of U-bottom microtiter plates (BD Diagnostic Systems; Catalog No. 353077) with and without 1-butanol to identify 1-butanol-tolerant isolates. The isolates were challenged separately with 2.0% and 3.0% w/v of 1-butanol. Butanol tolerance was determined by growth in the presence of 1-butanol as determined by measuring increases in optical density at 595 nm ($OD_{595}$) on a microtiter plate reader (HTS 7000 Plus Bio Assay Reader, PerkinElmer Life and Analytical Sciences Inc., Wellesley, Mass.). Isolates that had $OD_{595}$ readings in the range of 0.1 to 0.8 after growth for 48 h at 37° C. with shaking were selected for further tolerance testing. Alternatively, isolates from the master plate were replica-plated onto S20 agar containing up to 3.4% 1-butanol using the Nunc-TSP transferable solid phase screening system (Nalgene Nunc International, Naperville, Ill.; Catalog No. 445-497). Tolerant isolates were identified by growth at 37° C. after 24 to 72 h. Several isolates, including those listed in Table 5, displayed growth in 2.5% or higher 1-butanol on a solid medium. The $IC_{50}$ values of the isolated strains were determined at 37° C., for 1-butanol, 2-butanol, isobutanol, 2-butanone (also called methyl ethyl ketone (MEK)) and ethanol, following the method described in Example 1. The results are summarized in Table 5. Based on the $IC_{50}$ values determined for each compound and a correlation seen between tolerance to 1-btuanol and to each of the other tested compounds, the identified tolerant strains are expected to grow on solid medium containing 3.9% w/v 2-butanol, 2.7% w/v isobutanol, 5.0% w/v 2-butanone, or 9.0% w/v ethanol.

The isolates were identified by sequencing the 16S rRNA genes, as described in Example 1. The SEQ ID for each isolate's 16S rRNA, the phylotype, and the isolate designations are also given in Table 5.

TABLE 5

Butanol Tolerant Bacterial Strains Isolated from Environmental Samples using Continuous Culture

| Isolate | Phylotype | 16S rRNA Sequence | $IC_{50}$ (%) 1-butanol | $IC_{50}$ (%) 2-butanol | $IC_{50}$ (%) iso-butanol | $IC_{50}$ (%) 2-butanone | $IC_{50}$ (%) Ethanol |
|---|---|---|---|---|---|---|---|
| PN0048 | Enterococcus gallinarium | SEQ ID NO: 42 | 1.7 | 2.6 | 1.8 | 3.6 | 4.4 |
| PN0197-10 | Enterococcus faecalis | SEQ ID NO: 43 | 1.8 | 2.9 | 1.8 | 3.2 | 4.1 |
| PN0133 | Enterococcus faecium | SEQ ID NO: 44 | 1.9 | 2.8 | 2.1 | 3.0 | 4.4 |

What is claimed is:

1. An isolated butanol tolerant *Enterococcus* having the following characteristics:
   i) is a facultative anaerobe; and
   ii) is Gram-positive; and
   iii) is non-motile; and
   iv) has spherical or ovoid cell morphology; and
   v) has ability to initiate growth in a broth comprising 6.5% sodium chloride; and
   vi) has the ability to initiate growth in broth at pH 9.6; and
   vii) is tolerant to at least 2.5% w/v butanol when grown on a solid medium, wherein the butanol tolerant *Enterococcus* comprises a 16S rRNA gene having a sequence selected from the group consisting of SEQ ID NO:41, SEQ ID NO:42, SEQ ID NO:43, and SEQ ID NO:44.

2. The isolated butanol tolerant *Enterococcus* of claim 1 for use in the production of butanol.

* * * * *